United States Patent
Eppstein et al.

(10) Patent No.: US 8,517,958 B2
(45) Date of Patent: *Aug. 27, 2013

(54) TRANSDERMAL INTEGRATED ACTUATOR DEVICE, METHODS OF MAKING AND USING SAME

(75) Inventors: Jonathan Eppstein, Atlanta, GA (US); Stuart McRae, Atlanta, GA (US)

(73) Assignee: Nitto Denko Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/944,792

(22) Filed: Nov. 12, 2010

(65) Prior Publication Data
US 2011/0245728 A1   Oct. 6, 2011

Related U.S. Application Data

(63) Continuation of application No. 10/384,763, filed on Mar. 11, 2003, now abandoned, which is a continuation-in-part of application No. 09/590,787, filed on Jun. 8, 2000, now Pat. No. 6,692,456.

(60) Provisional application No. 60/363,022, filed on Mar. 11, 2002.

(51) Int. Cl.
*A61B 5/15* (2006.01)
*A61B 18/18* (2006.01)
*A61M 37/00* (2006.01)

(52) U.S. Cl.
USPC ............................... 600/575; 604/20; 606/45

(58) Field of Classification Search
USPC ............... 604/19, 20, 22, 46, 47, 48; 606/20, 606/45; 600/575
See application file for complete search history.

(56) References Cited

U.S. PATENT DOCUMENTS

| | | | |
|---|---|---|---|
| 3,551,554 A | 12/1970 | Herschler | |
| 3,711,602 A | 1/1973 | Herschler | |
| 3,711,606 A | 1/1973 | Herschler | |
| 3,964,482 A | 6/1976 | Gerstel et al. | |
| 4,340,048 A | 7/1982 | Eckenhoff | |
| 4,522,622 A | 6/1985 | Peery et al. | |
| 4,537,776 A | 8/1985 | Cooper | |
| 4,557,943 A | 12/1985 | Rosler et al. | |
| 4,758,081 A | 7/1988 | Barnes | |

(Continued)

FOREIGN PATENT DOCUMENTS

| | | |
|---|---|---|
| EP | 0 497 620 | 8/1992 |
| EP | 0 506 632 | 9/1992 |
| EP | 0 514 258 | 11/1992 |
| GB | 2 153 233 | 8/1985 |

(Continued)

OTHER PUBLICATIONS

"After bite's unique formula key to efficacy" news release (no author), Tender Corporation, Littleton, NH, Aug. 1994.

(Continued)

*Primary Examiner* — Kevin C Sirmons
*Assistant Examiner* — Michael J Anderson
(74) *Attorney, Agent, or Firm* — King & Spalding

(57) ABSTRACT

The invention provides for an integrated device for forming a cavity in a surface of a tissue of an animal comprising:
  a) a controller board connected to an energy source for actuating at least one porator;
  b) a fluid reservoir in fluid communication with the tissue; and
  c) a tissue interface layer, the tissue interface layer containing the at least one porator, the porator in contact with the tissue for forming the cavity.

The invention also provides for methods of making and methods of using the same.

16 Claims, 34 Drawing Sheets

(56) References Cited

U.S. PATENT DOCUMENTS

| | | |
|---|---|---|
| 4,764,164 A | 8/1988 | Sasaki |
| 4,767,402 A | 8/1988 | Kost et al. |
| 4,775,361 A | 10/1988 | Jacques et al. |
| 4,820,720 A | 4/1989 | Sanders et al. |
| 4,844,098 A | 7/1989 | Mitchen |
| 4,855,298 A | 8/1989 | Yamada et al. |
| 4,860,743 A | 8/1989 | Abela |
| 4,863,970 A | 9/1989 | Patel et al. |
| 4,921,475 A | 5/1990 | Sibalis |
| 4,942,883 A | 7/1990 | Newman |
| 4,973,468 A | 11/1990 | Chiand et al. |
| 5,003,987 A | 4/1991 | Grinwald |
| 5,006,342 A | 4/1991 | Cleary et al. |
| 5,016,615 A | 5/1991 | Driller et al. |
| 5,019,034 A | 5/1991 | Weaver et al. |
| 5,041,109 A | 8/1991 | Abela |
| 5,092,864 A | 3/1992 | Hayes et al. |
| 5,115,805 A | 5/1992 | Bommannan et al. |
| 5,137,817 A | 8/1992 | Busta et al. |
| 5,139,023 A | 8/1992 | Stanley et al. |
| 5,165,418 A | 11/1992 | Tankovich |
| 5,169,389 A | 12/1992 | Kriesel |
| 5,171,215 A | 12/1992 | Flanagan |
| 5,190,558 A | 3/1993 | Ito |
| 5,215,520 A | 6/1993 | Shroot et al. |
| 5,223,219 A | 6/1993 | Subramanian et al. |
| 5,224,928 A | 7/1993 | Sibalis et al. |
| 5,226,907 A | 7/1993 | Tankovich |
| 5,231,975 A | 8/1993 | Bommannan et al. |
| 5,246,437 A | 9/1993 | Abela |
| 5,250,023 A | 10/1993 | Lee et al. |
| 5,267,985 A | 12/1993 | Shimada et al. |
| 5,273,525 A | 12/1993 | Hofmann |
| 5,279,544 A | 1/1994 | Gross et al. |
| 5,318,514 A | 6/1994 | Hofmann |
| 5,323,769 A | 6/1994 | Bommannan et al. |
| 5,328,453 A | 7/1994 | Sibalis |
| 5,342,355 A | 8/1994 | Long |
| 5,362,307 A | 11/1994 | Guy et al. |
| 5,380,272 A | 1/1995 | Gross |
| 5,421,816 A | 6/1995 | Lipkovker |
| 5,423,803 A | 6/1995 | Tankovich et al. |
| 5,425,728 A | 6/1995 | Tankovich |
| 5,427,585 A | 6/1995 | Bettinger |
| 5,445,609 A | 8/1995 | Lattin et al. |
| 5,445,611 A | 8/1995 | Eppstein et al. |
| 5,458,140 A | 10/1995 | Eppstein et al. |
| 5,459,127 A | 10/1995 | Felgner et al. |
| 5,462,520 A | 10/1995 | Hofmann |
| 5,547,467 A | 8/1996 | Pliquett et al. |
| 5,548,140 A | 8/1996 | Nguyen et al. |
| 5,554,153 A | 9/1996 | Costello et al. |
| 5,580,859 A | 12/1996 | Felgner et al. |
| 5,582,586 A | 12/1996 | Tachibana et al. |
| 5,611,806 A | 3/1997 | Jang |
| 5,651,768 A | 7/1997 | Sibalis |
| 5,697,901 A | 12/1997 | Eriksson |
| 5,713,845 A | 2/1998 | Tankovich |
| 5,722,397 A | 3/1998 | Eppstein |
| 5,752,949 A | 5/1998 | Tankovich et al. |
| 5,801,057 A | 9/1998 | Smart et al. |
| 5,817,089 A | 10/1998 | Tankovich et al. |
| 5,879,326 A | 3/1999 | Godshall et al. |
| 5,882,317 A | 3/1999 | Saito et al. |
| 5,885,211 A | 3/1999 | Eppstein et al. |
| 5,925,035 A | 7/1999 | Tankovich |
| 5,947,921 A | 9/1999 | Johnson et al. |
| 5,983,136 A | 11/1999 | Kamen |
| 6,013,318 A | 1/2000 | Hunt et al. |
| 6,022,316 A | 2/2000 | Eppstein et al. |
| 6,027,459 A | 2/2000 | Shain et al. |
| 6,048,337 A | 4/2000 | Svedman |
| 6,050,988 A | 4/2000 | Zuck |
| 6,056,738 A | 5/2000 | Marchitto et al. |
| 6,071,249 A | 6/2000 | Cunningham et al. |
| 6,071,251 A | 6/2000 | Cunningham et al. |
| 6,083,196 A | 7/2000 | Trautman et al. |
| 6,117,290 A | 9/2000 | Say et al. |
| 6,138,044 A | 10/2000 | Svedman |
| 6,142,939 A | 11/2000 | Eppstein et al. |
| 6,148,232 A | 11/2000 | Avrahami |
| 6,173,202 B1 | 1/2001 | Eppstein |
| 6,183,434 B1 | 2/2001 | Eppstein |
| 6,230,051 B1 | 5/2001 | Cormier et al. |
| 6,247,485 B1 | 6/2001 | Rossi et al. |
| 6,251,083 B1 | 6/2001 | Yum et al. |
| 6,290,991 B1 | 9/2001 | Roser et al. |
| 6,334,856 B1 | 1/2002 | Allen et al. |
| 6,352,506 B1 | 3/2002 | Eppstein et al. |
| 6,451,240 B1 | 9/2002 | Sherman et al. |
| 6,508,785 B1 | 1/2003 | Eppstein |
| 6,527,716 B1 | 3/2003 | Eppstein |
| 6,659,982 B2 | 12/2003 | Douglas et al. |
| 6,692,456 B1 | 2/2004 | Eppstein et al. |
| 6,708,060 B1 | 3/2004 | Avrahami et al. |
| 6,711,435 B2 | 3/2004 | Avrahami |
| 6,730,028 B2 | 5/2004 | Eppstein et al. |
| 6,887,202 B2 | 5/2005 | Currie et al. |
| 6,906,540 B2 | 6/2005 | McQuade |
| 7,041,057 B1 | 5/2006 | Faupel et al. |
| 7,048,723 B1 | 5/2006 | Frazier |
| 7,070,590 B1 | 7/2006 | Santini |
| 7,108,681 B2 | 9/2006 | Gartstein |
| 7,131,987 B2 | 11/2006 | Sherman |
| 7,141,034 B2 | 11/2006 | Eppstein et al. |
| 7,392,080 B2 | 6/2008 | Eppstein et al. |
| 7,758,561 B2 | 7/2010 | Eppstein |
| 2002/0010414 A1 | 1/2002 | Coston et al. |
| 2002/0131994 A1 | 9/2002 | Schur et al. |
| 2003/0078499 A1 | 4/2003 | Eppstein |
| 2003/0092982 A1 | 5/2003 | Eppstein |
| 2003/0097127 A1 | 5/2003 | Avrahami |
| 2004/0039342 A1 | 2/2004 | Eppstein |
| 2004/0220456 A1 | 11/2004 | Eppstein |
| 2005/0165393 A1 | 7/2005 | Eppstein |
| 2009/0264810 A1 | 10/2009 | Eppstein |

FOREIGN PATENT DOCUMENTS

| | | |
|---|---|---|
| GB | 2 221 393 | 2/1990 |
| WO | WO 92/00106 | 1/1992 |
| WO | WO 93/07801 | 4/1993 |
| WO | WO 93/20745 | 10/1993 |
| WO | WO 94/08655 | 4/1994 |
| WO | WO 94/09713 | 5/1994 |
| WO | WO 95/10223 | 4/1995 |
| WO | WO 96/00110 | 1/1996 |
| WO | WO 96/17648 | 6/1996 |
| WO | WO 96/41657 | 12/1996 |
| WO | WO 97/04832 | 2/1997 |
| WO | WO 97/07734 | 3/1997 |
| WO | WO 98/00193 | 1/1998 |
| WO | WO 98/22719 | 5/1998 |
| WO | WO 98/29134 | 7/1998 |
| WO | WO 99/29364 | 6/1999 |
| WO | WO 99/40848 | 8/1999 |
| WO | WO 99/43350 | 9/1999 |
| WO | WO 99/44507 | 9/1999 |
| WO | WO 99/44508 | 9/1999 |
| WO | WO 99/44637 | 9/1999 |
| WO | WO 99/44638 | 9/1999 |
| WO | WO 99/44678 | 9/1999 |
| WO | WO 00/03758 | 1/2000 |
| WO | WO 00/04821 | 2/2000 |
| WO | WO 00/04832 | 2/2000 |
| WO | WO 00/15102 | 3/2000 |
| WO | WO 00/27473 | 5/2000 |
| WO | WO 00/74767 | 12/2000 |
| WO | WO 02/056939 | 7/2002 |
| WO | WO 03/077970 | 9/2003 |

OTHER PUBLICATIONS

Gustin et al. "Effects of Atmospheric Ammonia on Pulmonary Hemodynamic and Vascular Permeability in Pigs: Interactions with Endiotoxins," *Toxicology and Applied Pharmacology* 125:17-26 (1994).

Jacques et al. "Controlled Removal of Human Stratum Corneum by Pulsed Laser," *J. Invest. Dermatol*. 88:88-93 (1987).

Lane et al., "Ultraviolet-laser Ablation of Skin," *Arch Dermatol*. 121:609-617 (1985).

Matsumoto "Effects of ammonia and histamine on lung irritant receptors in the rabbit," *Respiratory Physiology* 77:301-308 (1989).

Matsumoto et al. "Substance P Antagonist Does Not Block the Stimulation of Rapidly Adapting Pulmonary Stretch Receptors by Ammonia", *Lung* 172:31-45 (1994).

McClung et al. "Early Changes in the Permeability of the Blood-Brain Barrier Produced by Toxins Associated with Liver Failure," *Pediatric Research 28 No. 3* 227-231 (1990).

Pohl et al. "Microjet assisted dye-enhanced diode laser ablation of cartilaginous tissue" *SPIE* vol. 2134A of *Laser-Tissue Interaction* (1994) at pp. 1326-1328.

Santus et al. "Transdermal enhancer patent literature" *J. Control Release* 25:1-20 (1993).

Ueda et al. "Skin penetration-enhancing effect of drugs by phonophoresis" *J of Controlled Release*. vol. 37:291-297 (1995).

Zaki et al. "Potential Toxins of acute liver failure and their effects on blood brain permeability," *Experientia* 39, Birkhäuser Verlag, CH-4010 Basel/Switzerland:988-991 (1983).

Ziylan et al. "Changes in the permeability of the blood brain barrier in acute hyperammonemia. Effect of dexamethasone" *Mol Chem Neurpathol* 20:203-218 (1993).

Extended European Search Report for EP Patent Application No. 10185373 issued on Jul. 1, 2011.

Extended European Search Report for EP Patent Application No. 10182248 issued on Mar. 15, 2011.

FIG. 8 a, b and c

FIG. 10 a, b and c

FIG. 11a, b, c and d

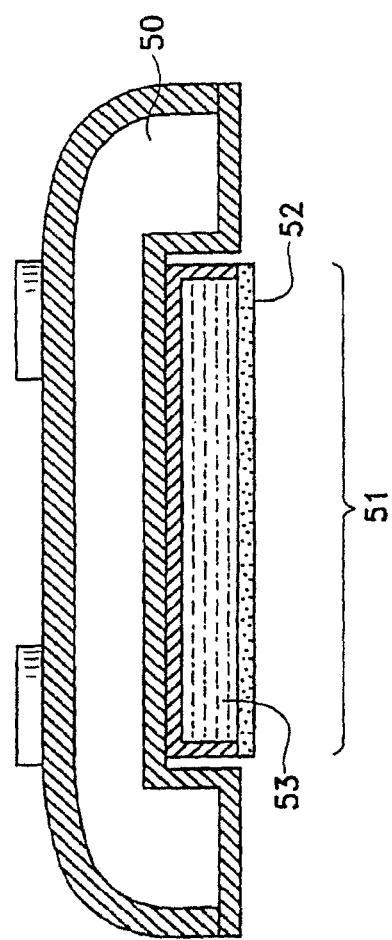

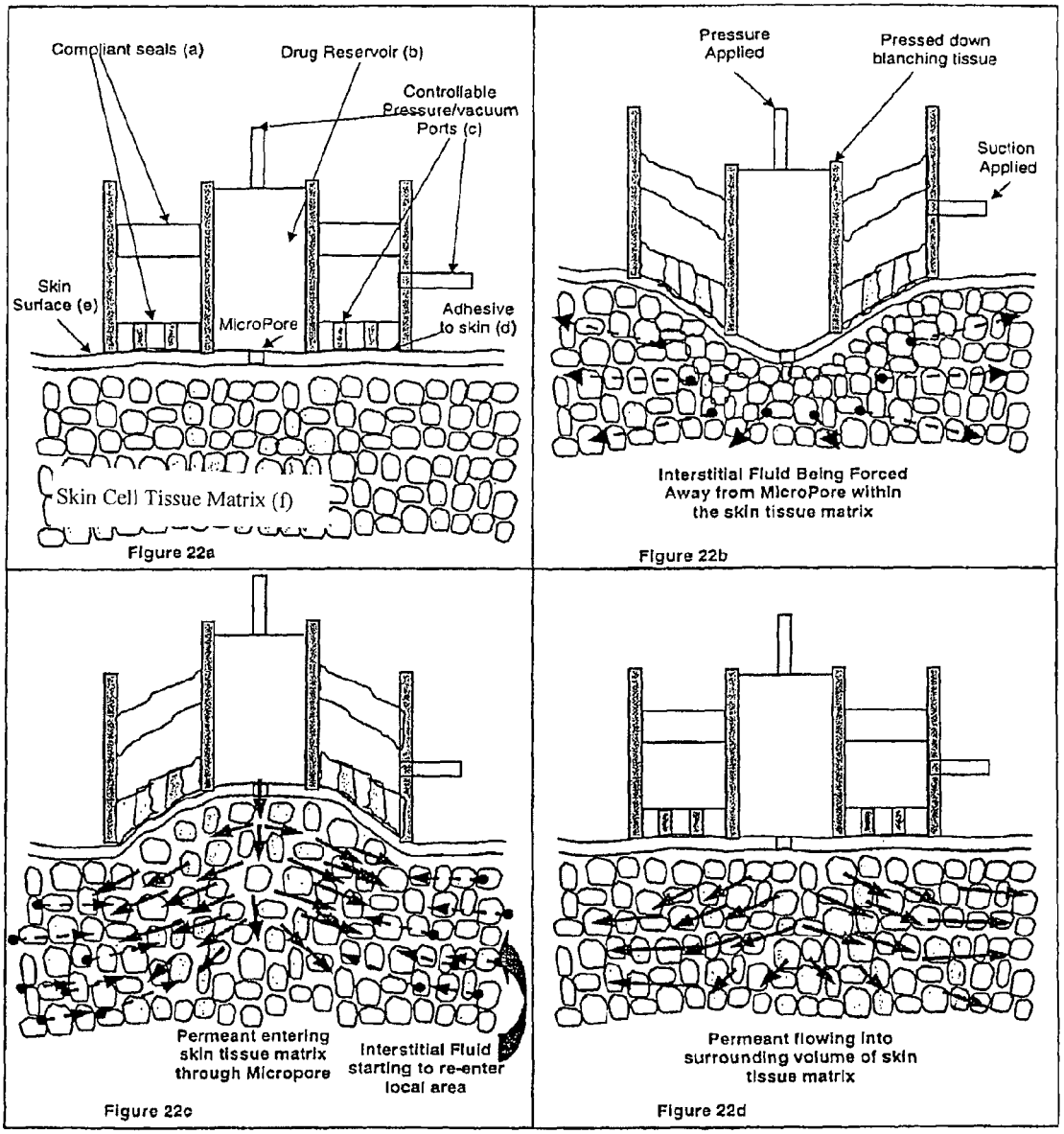

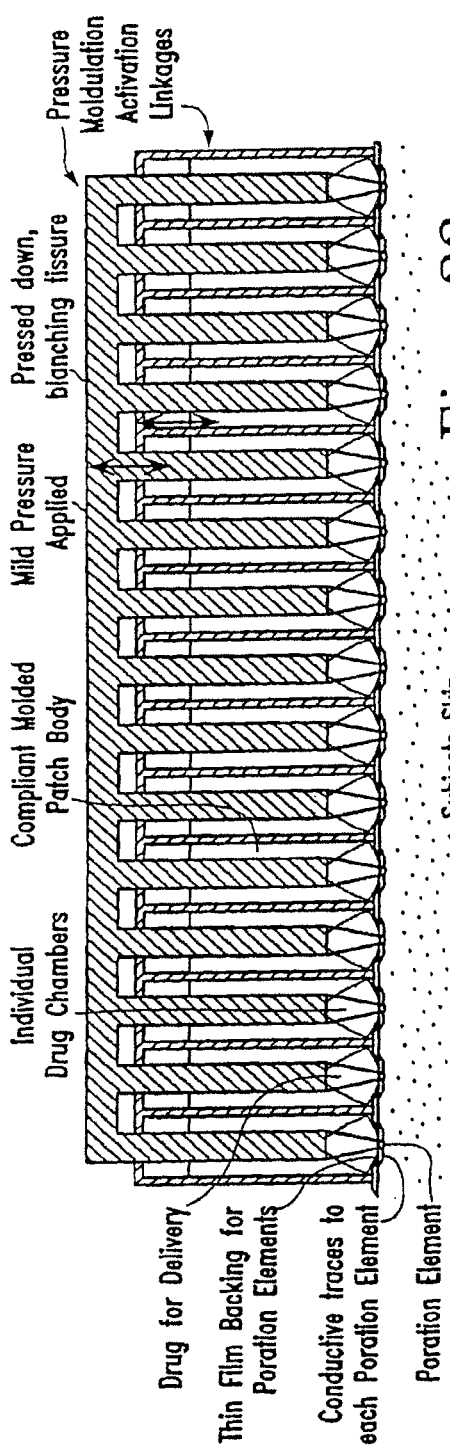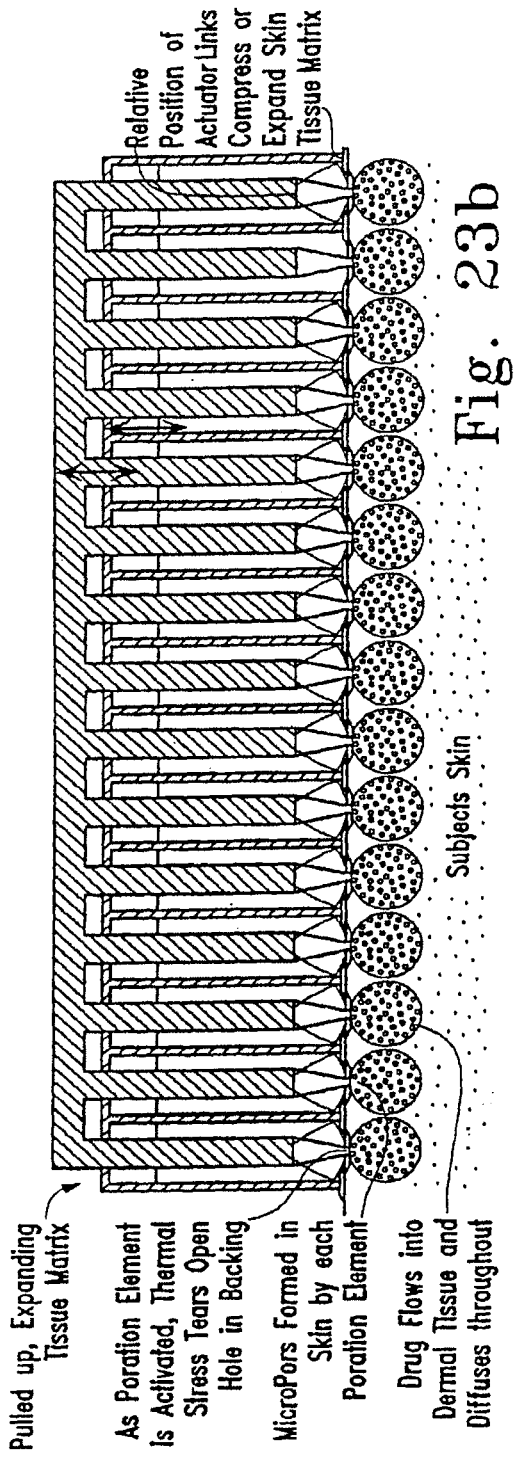

TRANSDERMAL INTEGRATED ACTUATOR DEVICE, METHODS OF MAKING AND USING SAME

CROSS REFERENCE TO RELATED APPLICATIONS

This application is a continuation of co-pending U.S. application Ser. No. 10/384,763, filed Mar. 11, 2003, which claims priority to U.S. Provisional Application No. 60/363,022, filed Mar. 11, 2002, and which is a continuation-in-part of U.S. application Ser. No. 09/590,787, filed Jun. 8, 2000, now U.S. Pat. No. 6,692,456. The complete disclosure for each of the above-identified appliance is hereby fully incorporated herein by reference.

TECHNICAL FIELD

This invention relates to devices and method for the creation of small holes or perforations or micropores in biological membranes, such as the outer layers of the skin or the mucosal linings, the delivery of drugs or other permeants through the micropores, the extraction of biological fluids through the micropores, the integration within the device and method of an assay for selected of analytes in the extracted biological fluids, and the increase of flux through these micropores by one or more of pressure modulation, the mechanical manipulation or distortion of the microporated tissue and adjacent tissue, electro-transport, electro-osmosis, iontophoresis and sonic energy. All publications, patents and patent applications referred to herein are incorporated herein by reference in their entirety.

BACKGROUND ART

The stratum corneum is chiefly responsible for the barrier properties of skin. Thus, it is this layer that presents the greatest barrier to transdermal flux of drugs or other molecules into the body and of analytes out of the body. The stratum corneum, the outer horny layer of the skin, is a complex structure of compact keratinized cell remnants separated by lipid domains. Compared to the oral or gastric mucosa, the stratum corneum is much less permeable to molecules either external or internal to the body. The stratum corneum is formed from keratinocytes, which comprise the majority of epidermal cells that lose their nuclei and become corneocytes. These dead cells comprise the stratum corneum, which has a thickness of only about 10-30 microns and, as noted above, is a very resistant waterproof membrane that protects the body from invasion by exterior substances and the outward migration of fluids and dissolved molecules. The stratum corneum is continuously renewed by shedding of corneum cells during desquamination and the formation of new corneum cells by the keratinization process.

Historically, drugs have been delivered across the skin by injection. However, this method of administration is inconvenient and uncomfortable, and is not suited for self-administration by members of the general public. Additionally, used needles continue to pose a hazard after their use. Therefore, transdermal drug delivery to the body is particularly desired.

There are many techniques known in the art for transdermal drug delivery and monitoring applications. One well-known example of the need in the art for less painful puncturing of a biological membrane is in the field of diabetes monitoring. The current standard of care for a patient with diabetes includes a recommendation of 3 to 5 painful finger-stick blood draws per day to allow them to monitor their blood glucose levels. Other than the relative size of the lancets decreasing over the last few years, the use of lancets, and the resulting finger sensitivity and pain, has not changed for many years.

To enhance transdermal drug delivery, there are known methods for increasing the permeability of the skin to drugs. For example, U.S. Pat. No. 5,885,211 is directed to thermal microporation techniques and devices to form one or more micropores in a biological membrane and methods for selectively enhancing outward flux of analytes from the body or the delivery of drugs into the body. PCT WO 00/03758, published Jan. 27, 2000 is directed to methods and apparatus for forming artificial openings in a selected area of a biological membrane using a pyrotechnic element that is triggered to explode in a controlled fashion so that the micro-explosion produces the artificial opening in the biological membrane to a desired depth and diameter. PCT WO98/29134, published Jul. 9, 1998 discloses a method of enhancing the permeability of a biological membrane, such as the skin of an animal, using microporation and an enhancer such as a sonic, electromagnetic, mechanical, thermal energy or chemical enhancer. Methods and apparatus for delivery or monitoring using microporation also are described in PCT WO 99/44637, published Sep. 10, 1999; U.S. Pat. No. 6,022,316; PCT WO 99/44508, published Sep. 10, 1999; PCT WO 99/44507, published Sep. 10, 1999; PCT WO 99/44638, published Sep. 10, 1999; PCT WO 00/04832, published Feb. 3, 2000; PCT WO 00/04821, published Feb. 3, 2000; and PCT WO 00/15102, published Mar. 23, 2000.

There remains a need for improved methods and devices for transdermal delivery of agents such as drugs and monitoring of analytes such as blood components.

SUMMARY OF THE INVENTION

This invention relates to an integrated device for forming a cavity in a surface of a tissue of an animal comprising: a) a controller board connected to an energy source for actuating at least one porator; b) a fluid reservoir in fluid communication with said tissue; and c) a tissue interface layer, said tissue interface layer containing said at least one porator, said porator in contact with said tissue for forming said cavity.

Another embodiment of the present inventive subject matter is directed to an integrated poration device comprising: a) a poration device comprising: i) an outer body defining a top of said poration device, said outer body containing a cavity; ii) a controller board comprising driving electronics and a battery, said controller board being positioned within said cavity; and iii) a tissue interface layer for contacting a tissue membrane of an animal, said tissue interface layer containing at least one porator, and said tissue interface layer forming the bottom of said poration device; and b) a reservoir patch, said reservoir patch being applied to said porated area of said tissue membrane after poration.

A further embodiment of the present inventive subject matter is directed to an integrated poration device comprising: a) an actuator comprising: i) an outer body defining a top of said actuator, said outer body containing a cavity; ii) a controller board comprising driving electronics and a battery, said controller board being positioned within said cavity; and iii) an interface connection port for receiving a porator array, said interface connection port containing an anode and a cathode; b) said porator array comprising: i) a top surface, with a removable adhesive attached to said top surface, said top surface containing two concentric electrical contact rings for contacting said interface connection port at said anode and said cathode upon removal of said adhesive layer; ii) a bottom surface comprising a tissue interface membrane, said tissue interface layer further comprising a substrate with at least one porator contained on or within said substrate, said bottom surface further comprising an adhesive layer for attaching said porator array to a tissue membrane; and iii) a release liner removably attached to said bottom surface; and c) a reservoir patch, said reservoir patch being applied to said microporated area of said tissue membrane after poration.

A still further embodiment of the present inventive subject matter is directed to a poration system comprising: a) a porator array comprising at least one porator; and b) an actuator comprising: i) an outer body defining a top of said actuator, said outer body containing a cavity; ii) a controller board comprising driving electronics and a battery, said controller board being positioned within said cavity; and iii) an interface connection port for receiving said porator array.

An even further embodiment of the present inventive subject matter is directed to An method of monitoring an analyte extracted from a patient and delivering a permeant composition to said patient, comprising the steps of: a) contacting a poration device to a tissue membrane of said patient, said poration device comprising: i) an outer body defining a top of said integrated poration device, said outer body containing a cavity; ii) a controller board comprising driving electronics and a battery, said controller board being positioned within said cavity; iii) a first reservoir comprising a top, side walls and a bottom, said top comprising a thin film top plate abutting a bottom of said controller board and fitting within said cavity; and iv) a tissue interface layer for contacting said tissue membrane, said tissue interface layer containing at least one porator array and a second reservoir, and said tissue interface layer forming the bottom of said first reservoir and of said integrated poration device; b) actuating poration of said tissue membrane using said at least one poration array in said poration device; c) extracting an analyte from said microporated tissue membrane by way of said at least one micropore array; d) analyzing said analyte to determine concentration of same within said tissue membrane; and e) delivering a permeant composition to said tissue membrane by way of said at least one micropore array.

A still even further embodiment of the present inventive subject matter is directed to a method of delivering two or more biologically active compounds to a patient in need thereof by way of a tissue membrane, said method comprising the steps of: a) forming at least one micropore in said tissue membrane by contacting a poration device with said tissue membrane and activating said poration device, thereby forming said at least one micropore, said poration device comprising: i) an outer body defining a top of said integrated poration device, said outer body containing a cavity; ii) a controller board comprising driving electronics and a battery, said controller board being positioned within said cavity; iii) a first reservoir comprising a top, side walls and a bottom, said top comprising a thin film top plate abutting a bottom of said controller board and fitting within said cavity; and iv) a tissue interface layer for contacting said tissue membrane, said tissue interface layer containing at least one porator array and a second reservoir, and said tissue interface layer forming the bottom of said first reservoir and of said integrated poration device; b) applying a first compound contained in said first reservoir of said poration device to said tissue membrane by way of said at least one micropore; and c) applying a second compound contained in said second reservoir of said poration device to said tissue membrane by way of said at least one micropore.

Furthermore, the present inventive subject matter is directed to a method of facilitating passage of biological compounds across a tissue membrane comprising the steps of: a) forming at least one micropore in said tissue membrane by contacting a poration device with said tissue membrane and activating said poration device, thereby forming said at least one micropore, said poration device comprising: i) an outer body defining a top of said integrated poration device, said outer body containing a cavity; ii) a controller board comprising driving electronics and a battery, said controller board being positioned within said cavity; iii) a first reservoir comprising a top, side walls and a bottom, said top comprising a thin film top plate abutting a bottom of said controller board and fitting within said cavity; and iv) a tissue interface layer for contacting said tissue membrane, said tissue interface layer containing at least one porator array and a second reservoir, and said tissue interface layer forming the bottom of said first reservoir and of said integrated poration device; b) applying a first compound contained in said first reservoir of said poration device to said tissue membrane by way of said at least one micropore; and c) extracting a second compound from said tissue membrane and storing said second compound in said second reservoir in said poration device.

Still further, the present inventive subject matter is directed to a method of manufacturing an integrated poration device comprising the steps of: a) forming an outer body defining a top of said integrated poration device, said outer body containing a cavity; b) assembling a controller board comprising driving electronics and a battery, and positioning said controller board within said cavity; c) assembling a reservoir comprising a top, side walls and a bottom, said top comprising a thin film top plate abutting a bottom of said controller board and positioning said reservoir within said cavity; and d) forming a tissue interface layer along the bottom of said reservoir, said tissue interface layer contacting a tissue membrane of an animal and containing at least one porator, and said tissue interface layer forming the bottom of said reservoir and of said integrated poration device.

Yet still further, the present inventive subject matter is directed to an integrated poration device comprising: a) an outer body defining a top of said integrated poration device, said outer body containing a cavity; b) a controller board comprising driving electronics and a battery, said controller board being positioned within said cavity; c) a reservoir comprising a top, side walls and a bottom, said top comprising a thin film top plate abutting a bottom of said controller board and fitting within said cavity; and d) a tissue interface layer for contacting a tissue membrane of an animal, said tissue interface layer containing at least one porator, and said tissue interface layer forming the bottom of said reservoir and of said integrated poration device.

BRIEF DESCRIPTION OF THE FIGURES

FIG. 20 shows one embodiment of an integrated device where one component of the device is reusable and the other component is disposable.

FIG. 22 shows cross sectional view of an embodiment of a mechanically actuated pressure modulation device for transcutaneous drug delivery or analyte monitoring applications.

FIG. 23 shows cross-sectional views of a pressure modulation device before activation of poration elements and after activation of poration elements and actuation of pressure modulation.

DETAILED DESCRIPTION

Definitions

Figure 1:
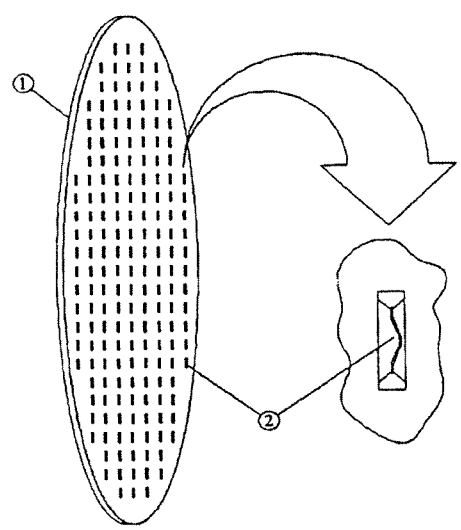
FIG. 1 is a general embodiment of a Thin Film Tissue Interface (TFTI) device showing an enlarged view of a single resistive element.

As used herein, "stratum corneum" refers to the outermost layer of the skin, consisting of from about 15 to about 20 layers of cells in various stages of drying out. The stratum corneum provides a barrier to the loss of water from inside the body to the external environment and from attack from the external environment to the interior of the body.

As used herein, "tissue" refers to an aggregate of cells of a particular kind, together with their intercellular substance, that forms a structural material. At least one surface of the tissue must be accessible to the device. The preferred tissue is the skin. Other tissues suitable for use with this invention include mucosal tissue and soft organs.

As used herein, the term, "interstitial fluid" is the clear fluid that occupies the space between the cells in the body. As used herein, the term "biological fluid" is defined as a fluid originating from a biological organism, including blood serum or whole blood as well as interstitial fluid.

As used herein, "poration," "microporation," or any such similar term means the formation of a small hole or crevice in (defined herein as a "micropore") or through the biological membrane, such as skin or mucous membrane, or the outer layer of an organism to lessen the barrier properties of this biological membrane the passage of biological fluids, such as analytes from below the biological membrane for analysis or the passage of active permeants or drugs from without the biological membrane for selected purposes. Preferably the hole or "micropore" so formed is approximately 1-1000 microns in diameter and would extend into the biological membrane sufficiently to break the barrier properties of the stratum corneum without adversely affecting the underlying tissues. It is to be understood that the term "micropore' is used in the singular form for simplicity, but that the device of the present invention may form multiple artificial openings. Poration could reduce the barrier properties of a biological membrane into the body for selected purposes, or for certain medical or surgical procedures. For the purposes of this application, "poration" and "microporation" are used interchangeably and mean the same thing.

A "microporator" or "porator" is a component for a microporation device capable of microporation. Examples of a microporator or porator include, but are not limited to, a heated probe element capable of conductively delivering thermal energy via direct contact to a biological membrane to cause the ablation of some portion of the membrane deep enough to form a micropore the heated probe may be comprised of an electrically heated resistive element capable of ablating a biological membrane or an optically heated topical dye/absorber layer, electro-mechanical actuator, a microlancet, an array of microneedles or lancets, a sonic energy ablator, a laser ablation system, and a high pressure fluid jet puncturer. As used herein, "microporator" and "porator" are used interchangeably.

As used herein "penetration" means the controlled removal of cells caused by the thermal and kinetic energy released when the pyrotechnic element explodes which causes cells of the biological membrane and possibly some adjacent cells to be "blown away" from the site. As used herein, "fusible" and "fuse" refer to an element that could remove itself from and electrical circuit when a sufficient amount of energy or heat has been applied to it. i.e., when a resistive, electrically activated poration element is designed to be a fusible element this means that upon activation, during or after the formation of the micropore in the biological membrane, the element breaks, stopping the current flow through it.

As used herein, "penetration enhancement" or "permeation enhancement" means an increase in the permeability of the biological membrane to a drug, analyte, or other chemical molecule, compound, particle or substance (also called "permeant"), i.e., so as to increase the rate at which a drug, analyte, or other chemical molecule, compound or particle permeates the biological membrane and facilitates the increase of flux across the biological membrane for the purpose of the withdrawal of analytes out through the biological membrane or the delivery of drugs across the biological membrane and into the underlying tissues.

As used herein, "enhancer", "chemical enhancer," "penetration enhancer", "permeation enhancer," and the like includes all enhancers that increase the flux of a permeant, analyte, or other molecule across the biological membrane, and is limited only by functionality. In other words, all cell envelope disordering compounds and solvents and any other chemical enhancement agents are intended to be included. Additionally, all active force enhancer technologies such as the application of sonic energy, mechanical suction, pressure, or local deformation of the tissues, iontophoresis or electroporation are included. For example, ammonia may be used as an enhancer for the device of the present invention. In this example, the ammonia may increase the permeability of selected tissue structures, such as the capillary walls, within the tissues proximate to, or extending some distance from, the formed micropore. One or more enhancer technologies may be combined sequentially or simultaneously. For example, the ammonia enhancer may first be applied to permealize the capillary wall and then an iontophoretic or sonic energy field may be applied to actively drive a permeant into those tissues surrounding and comprising the capillary bed. The shock wave generated by the detonation of the pyrotechnic element of the present invention is itself a sonic permeation enhancer.

As used herein, "transdermal" or "percutaneous" means passage of a permeant into and through the biological membrane to achieve effective therapeutic blood levels or local tissue levels of a permeant, or the passage of a molecule or fluid present in the body ("analyte") out through the biological membrane so that the analyte molecule maybe collected on the outside of the body.

As used herein, the term "permeant," "drug," "permeant composition," or "pharmacologically active agent" or any other similar term means any chemical or biological material or compound suitable for transdermal administration by the methods previously known in the art and/or by the methods taught in the present invention, that induces a desired biological or pharmacological effect, which may include but is not limited to (1) having a prophylactic effect on the organism and preventing an undesired biological effect such as an infection, (2) alleviating a condition caused by a disease, for example, alleviating pain or inflammation caused as a result of disease, and/or (3) either alleviating, reducing, or completely eliminating the disease from the organism. The effect may be local, such as providing for a local anesthetic effect, or it may be systemic. Such substances include broad classes of compounds normally delivered into the body, including through body surfaces and membranes, including skin. In general, this includes but is not limited to: anti-infectives such as antibiotics and antiviral agents; analgesics and analgesic combinations; anorexics; antihelminthics; antiarthritics; antiasthmatic agents; anticonvulsants; antidepressants; antidiabetic agents; antidiarrheals; antihistamines; anti-inflammatory agents; antimigraine preparations; antinauseants; antineoplastics; antiparkinsonism drugs; antipruritics; antipsychotics; antipyretics; antispasmodics; anticholinergics; sympathomimetics; xanthine derivatives; cardiovascular preparations including potassium and calcium channel blockers, beta-blockers, alpha-blockers and. antiarrhythmics; antihypertensives; diuretics and antidiuretics; vasodilators including general coronary, peripheral and cerebral; central nervous system stimulants; vasoconstrictors; cough and cold preparations, including decongestants; hormones such as estradiol and other steroids, including corticosteroids; hypnotics; immunosuppressives; muscle relaxants; parasympatholytics; psychostimulants; sedatives; and tranquilizers. By the method of the present invention, both ionized and nonionized drugs maybe delivered, as could drugs of either high or low molecular weight. Additionally, microparticles, DNA, RNA, viral antigens or any combination of the permeants listed above may be delivered by the present invention. Examples include polypeptides, including proteins and peptides (e.g., insulin); releasing factors, including Luteinizing Hormone Releasing Hormone (LHRH); and carbohydrates (e.g., heparin). Ionized and nonionized permeants may be delivered, as could permeants of any molecular weight including substances with molecular weights ranging from less than 50 Daltons to greater than 1,000,000 Daltons.

As used herein, an "effective" amount of a pharmacologically active agent means a sufficient amount of a compound to provide the desired local or systemic effect and performance at a reasonable benefit/risk ratio attending any medical treatment. An "effective" amount of a permeation or chemical enhancer as used herein means an amount selected so as to provide the desired increase in biological membrane permeability, the desired depth of penetration, rate of administration, and amount of drug delivered.

As used herein, a "pyrotechnic element" means any chemical, matter or combination of chemicals and/or matters that have an explosive characteristic when suitably detonated. The pyrotechnic element of the present invention undergoes very rapid decomposition (as combustion) with the production of heat and the formation of more stable materials (as gases) which exert pressure as they expand at the high temperature produced thereby creating a shock wave with a high peak pressure lasting for a short period of time. Thus, the energy produced by the pyrotechnic element includes both high temperature and high pressure. One example of a pyrotechnic element suitable for the present invention includes a stoichiometric mixture of zirconium powder and potassium perchlorate combined with a nitrocellulose binder of 1-5 parts per 100 parts of the stoichiometric mixture as a suspension in an organic solvent. Another example would be a gelled form of nitroglycerin, which has the additional advantage of already being an approved drug for transdermal delivery applications.

As used herein, a "pyrotechnic ink" means any pyrotechnic element that is applied in a liquid form and which subsequently cures into the solid or gelled shape of the pyrotechnic element.

As used herein, the term "biological membrane" or "tissue membrane" means the structure separating one area of an organism from another, such as a capillary wall, lining of the gut or the outer layer of an organism which separates the organism from it's external environment, such as epithelial tissue, skin, buccal mucosa or other mucous membrane. The stratum corneum of the skin may also be included as a biological membrane.

As used herein, "animal" or "organism" refers to humans and other living organisms including plants, to which the present invention maybe applied.

As used herein, "analyte" means any chemical or biological material or compound suitable for passage through a biological membrane by the technology taught in this present invention, or by technology previously known in the art, of which an individual might want to know the concentration or activity inside the body. Glucose is a specific example of an analyte because it is a sugar suitable for passage through the skin, and individuals, for example those having diabetes, might want to know their blood glucose levels. Other examples of analytes include, but are not limited to, such compounds as sodium, potassium, bilirubin, urea, ammonia, calcium, lead, iron, lithium, salicylates, and the like.

As used herein, "transdermal flux rate" is the rate of passage of any analyte out through the skin of an individual, human or animal, or the rate of passage of any permeant, drug, pharmacologically active agent, dye, or pigment in and through the skin of an organism.

As used herein, "artificial opening" or "micropore" means any physical breach of the biological membrane of a suitable size for delivering or extraction fluid therethrough, including micropores. "Artificial opening" or "micropore" or any such similar term thus refers to a small hole, opening or crevice created to a desired depth in or through a biological membrane. The opening could be formed via the conduction of thermal energy as described in U.S. Pat. No. 5,885,211, or through a mechanical process, or through a pyrotechnic process. The size of the hole or pore is for example approximately 1-1000 microns in diameter. It is to be understood that the term micropore is used in the singular form for simplicity, but that the devices and methods may form multiple openings or pores.

As used herein, "use" or "single use" is a single application of the device that could last for example, for a few seconds to a few days. An application is denoted by applying the device tissue interface to the tissue, the poration process, the delivery or extraction step, and the removal of the device tissue interface from the tissue. This "use" or "single use" could last for seconds, minutes, or days depending on the nature of the permeants delivered, the biological fluids extracted, and the flux rates desired.

"Iontophoresis" refers to the application of an external electric field to the tissue surface through the use of two or more electrodes and delivery of an ionized form of drug or an un-ionized drug carried with the water flux associated with ion transport (electro-osmosis) into the tissue or the similar extraction of a biological fluid or analyte.

"Electroporation" refers to the creation through electric current flow of openings in cell walls that are orders of magnitude smaller than micropores. The openings formed with electroporation are typically only a few nanometers in any dimension. Electroporation is useful to facilitate cellular uptake of selected permeants by the targeted tissues beneath the outer layers of an organism after the permeant has passed through the micropores into these deeper layers of tissue.

"Sonophoresis" or "sonification" refers to sonic energy, which may include frequencies normally described as ultrasonic, generated by vibrating a piezoelectric crystal or other electromechanical element by passing an alternating current through the material. The use of sonic energy to increase the permeability of the skin to drug molecules has been termed sonophoresis or phonophoresis.

"Integrated device" means a device suitable for forming artificial openings in tissue and further suitable for one or more additional applications, for example, delivering one or more permeants into the tissue (preferably through the artificial openings), and optionally collecting a biological fluid from the tissue (preferably through the artificial openings) and optionally analyzing the biological fluid to determine a characteristic thereof.

As used herein, "non-invasive" means not requiring the entry of a needle, catheter, or other invasive medical instrument into apart of the body.

As used herein, "minimally invasive" refers to the use of mechanical, hydraulic, or electrical means that invade the stratum corneum to create a small hole or micropore without causing substantial damage to the underlying tissues.

As used herein, "pharmaceutically acceptable carrier" refers to a carrier in which a substance such as a pharmaceutically acceptable drug could be provided for deliver. Pharmaceutically acceptable carriers are described in the art, for example, in "Remington: The Science and Practice of Pharmacy," Mack Publishing Company, Pennsylvania, 1995, the disclosure of which is incorporated herein by reference. Carriers could include, for example, water and other aqueous solutions, saccharides, polysaccharides, buffers, excipients, and biodegradable polymers such as polyesters, polyanhydrides, polyamino acids, liposomes and mixtures thereof.

As used herein, "reservoir" refers to a designated area or chamber within a device which is designed to contain a permeant for delivery through an artificial opening in a biological membrane into an organism or may be designed to receive a biological fluid sample extracted from an organism through an artificial opening in a biological membrane. A reservoir could also contain excipient compounds which enhance the effect of a separately contained bioactive permeant. Additionally. a reservoir could contain or be treated with reactive enzymes or reagents designed to allow the measurement or detection of a selected analyte in an extracted biological fluid. A reservoir may be comprised of a open volume space, a gel, a flat planar space which has been coated or treated with a selected compound for subsequent release or reaction, or a permeable solid structure such as a porous polymer.

The present invention comprises a device and a method for painlessly creating microscopic holes, i.e. micropores, from about 1 to 1000 microns across, in the stratum corneum of human skin. The device uses thermal energy source, or heat probe, which is held in contact with the stratum corneum, for creating micropores. The thermal micropores are created using short time-scale (1 microsecond to 50 milliseconds), thermal energy pulses to ablate the tissue of biological membranes. This process is described in detail in U.S. Pat. No. 5,885,211 and is hereby included in its entirety by reference.

The present invention facilitates a rapid and painless method of eliminating the barrier function of the stratum corneum to facilitate the transcutaneous transport of therapeutic substances into the body when applied topically or to access the analytes within the body for analysis. The method utilizes a procedure that begins with the contact application of a small area heat source to the targeted area of the stratum corneum or other selected biological membrane.

The heat source has the following properties. First, the heat source must be sized such that contact with the biological membrane is confined to a small area, typically about 1 to 1000 µm in diameter. Second, it must have the capability to modulate the temperature of the stratum corneum at the contact point from ambient skin surface temperature levels (33° C.) to greater than 123° C. (preferably to a temperature greater than 400° C.) and then return to approximately ambient skin temperature with total cycle times within the 1 microsecond to 50 milliseconds range to minimize collateral damage to adjacent viable tissues and sensation to the subject individual. This modulation could be created electronically, mechanically, or chemically.

With the heat source placed in contact with the skin, it is cycled through a series of one or more modulations of temperature from an initial point of ambient skin temperature to a peak temperature in excess of 123° C. to approximately ambient skin temperature. To minimize or eliminate the subject's sensory perception of the microporation process, these pulses are limited induration, and the interpulse spacing is long enough to allow cooling of the viable tissue layers in the skin, and most particularly the enervated dermal tissues, to achieve a mean temperature of less than about 45° C. These parameters are based on the thermal time constants of the viable epidermal and dermal tissues (roughly 30-80 ms) located between the heat probe and the enervated tissue in the underlying dermis. The result of this application of pulsed thermal energy is that enough energy is conducted into the stratum corneum within the tiny target spot that the local temperature of this volume of tissue is elevated sufficiently higher than the vaporization point of the tissue-bound volatile components, such as water and lipids in the stratum corneum. As the temperature increases above 100° C., these volatile components of the stratum corneum (typically comprising 5% to 15% within the stratum corneum) within this localized spot, are induced to vaporize and expand very rapidly, causing a vapor-driven removal of those corneocytes in the stratum corneum located in proximity to this vaporization event. U.S. Pat. No. 4,775,361 teaches that a stratum corneum temperature of 123° C. represents a threshold at which this type of flash vaporization occurs. As subsequent pulses of thermal energy are applied, additional layers of the stratum corneum are removed until a micropore is formed through the stratum corneum down to the next layer of the epidermis, the stratum lucidum. By limiting the duration of the heat pulse to less than one thermal time constant of the epidermis and allowing any heat energy conducted into the epidermis to dissipate for a sufficiently long enough time, the elevation in temperature of the viable layers of the epidermis is minimal. This allows the entire microporation process to take place without any sensation to the subject and no damage to the underlining and surrounding tissues.

One embodiment of this invention relates to designs and manufacturing techniques suitable for creating a practical, low cost, Thin Film Tissue Interface (TFTI) device that creates micropores using thermal energy produced by the passage of electrical current through resistive elements and methods of manufacturing and functional operation of the TFTI devices. TFTI devices create one or more micropores on a wide range of biological membranes. TFTIs have applications that include thermal microporation of human skin for the enhancement of analyte monitoring and delivery of permeants such as a therapeutic drug or a tattoo dye.

TFTIs are characterized by their ability to rapidly and efficiently create a pattern or array of micropores on the surface of a biological membrane. The pattern may be any geometric spacing of micropores with pore densities as high as one pore every 0.2 square mm and covering a total porated area ranging from a few square millimeters to greater than several hundred square centimeters. TFTI devices are designed to be thin, flexible, conformable structures that form the interface between a biological membrane and the controller portion of the integrated device that supplies each poration element or electrode or other active component such as a piezo-transducer in the TFTI with the required electrical signal to effect the poration or other function of the TFTI such as, but not limited to, iontophoresis, sonophoresis, electroporation, or impedance measurement of the contacted tissue. TFTIs are flexible and able to conform to the shape of the targeted biological membranes. The TFTIs are fabricated to be very thin, light in weight, and integrated with a reservoir and are also connected to the controller, current source through an umbilical cable to allow a more user-friendly configuration. When one or more controllable active additional flux enhancement features are incorporated into the TFTI, such as, but not limited to, pressure modulation, mechanical manipulation, iontophoresis, electro-osmosis, sonophoresis or electroporation, the activation of this additional flux control feature could be controlled by the remote controller module either in a preprogrammed fashion, a user controlled fashion via inputs to the controller, or in an automatic, closed loop fashion wherein the rate of infusion of a permeant is modulated as a function of the measured level of a selected analyte within or other measurable property of the organism. The other measurable property could include heart rate, blood pressure, temperature, respiration and skin surface conductivity. For example, if would be very useful to control the rate of insulin infusion based on the real-time measurement of glucose concentrations in the interstitial fluid or serum of an organism. Alternatively, it may be desirable with some therapeutic compounds, particularly those with narrower therapeutic windows defining what an effective drug level is versus when the negative side effects become too intolerable, to modulate the infusion rates based on the measurable levels of this compound within the organism, thereby allowing a very accurate, and self adaptive method for achieving and maintaining the drug concentration within a desired therapeutic window regardless of patient body mass or metabolism. In the design and manufacture of the TFTI, many of the electrically conductive traces comprising the TFTI could be used to serve multiple functions. For example, the traces used to deliver the short pulses of current to the resistive poration elements to induce the thermal cycling, could also be used as electrodes for an iontophoretic or electroporation process, carried out after the micropores have been formed.

This invention relates to a microporation device, comprising at least one reservoir and a tissue interface comprising at least one microporator and a substrate, wherein the microporator is located on or within the substrate. In one embodiment, the substrate is selected from the group consisting of a woven material, a film, a supporting layer and a sheet. The woven material comprises conductive fibers and non-conductive fibers. In another embodiment, the substrate comprises perforations.

The microporator may be selected from the group consisting of a probe element capable of conductively delivering thermal energy via direct contact to a biological membrane to cause the ablation of some portion of the membrane deep enough to form a micropore, electro-mechanical actuator, a microlancet, an array of micro-needles or lancets, a sonic energy ablator, a laser ablation system, and a high pressure fluid jet puncturer; and the probe element could be selected from the group consisting of an electrically heated resistive element capable of ablating a biological membrane, an optically heated topical dye absorber layer and optically heated topical dye layer.

In some embodiments of the microporation device of this invention, the probe element could be selected from the group consisting of a preformed wire conductor, a deposited conductive material, a machined conductive material, a laser cut conductive material, an adhesive foil, an electroplated material, a screen-printed material and an etched conductive material. In some embodiments, the probe element could be destroyed while ablating the biological membrane.

In an embodiment of this invention, at least one microporator comprises multiple microporators. In another embodiment of the microporation device, the multiple microporators are probe elements.

The microporation device of this invention could comprise diodes for isolating the electrical circuits used for activating the probe elements. The microporation device could comprise two or more of the probe elements are connected in a parallel circuit configuration or a series circuit configuration or a combination thereof.

The microporation device could comprise a material near the microporator, wherein the material could be capable of producing an exothermic or endothermic reaction. The microporation device could comprise a micro actuator. The microactuator could be selected from the group consisting of electro-static microactuators, thermal bimorph microactuators, piezoelectric microactuators, electromagnetic microactuators, magneto-restrictive microactuators and shape memory alloy microactuators.

The microporation device could comprise an electronic circuitry and a power source: The probe element could comprise a conductive wire and the substrate could comprise a nonconductive fabric. The conductive wire could be woven in the non-conductive fabric.

The microporation device could comprise a plug material on the perforations. The plug material could comprise a volatile material. In one embodiment of the microporation device, the substrate could be embossed. The microporation device could comprise an enhancer material for enhancing transmembrane or transdermal transport of a fluid across the biological membrane.

The microporation device could comprise multiple chambers. The multiple chambers could comprise different substances. At least one of the multiple chambers could be disposed after a single use of the microporation device. The multiple chambers could comprise at least first and second chambers, the first chamber comprising a first substance and the second chamber comprising a second substance. The first and second substances could be first and second biologically active agents. The first substance could be a dry formulation pharmaceutically active agent, and the second substance could be a diluent for reconstituting the dry formulation into a pharmaceutically acceptable liquid or gel formulation.

The microporation device could be capable of transdermal delivery of a substance in the first chamber or withdrawal of an analyte transdermally into the second chamber. The microporation device could be capable of simultaneous transdermal delivery of a substance in the first chamber and withdrawal of an analyte transdermally into the second chamber. The substance could be insulin and the analyte could be glucose. The substances could be selected from the group consisting of bioactive peptides or proteins, therapeutic drugs, vaccines, pain medications, permeation enhancers and pH stabilizers. The different substances could be delivered by the microporation device in modulated amounts. At least one of the different substances could passively diffuse into the biological membrane. The substances, which could be the same or different, could be delivered simultaneously, sequentially, alternately, or any combination thereof. The different substances could be delivered by the microporation device into the organism in adjacent locations in the biological membrane such that the different substances could combine and mix once they are within the tissue matrix of the organism.

The microporation device could comprise an analyzer for detecting or quantitating the analyte. The microporation device could comprise a control module for controlling the delivery of the substance based on a quantitative value of the analyte detected by the analyzer.

The microporation device could comprise a divider or valve disposed between the first and second chambers that prevents mixture of the first and second substances until the divider could be removed or the valve could be opened. The divider could be a membrane. The first substance could be a pharmaceutically active agent, and the second substance could a pharmaceutically acceptable carrier.

The microporation device could comprise a flux enhancement microporation device, wherein the flux enhancement microporation device enhances a flux rate of a substance into the biological membrane. The flux enhancement microporation device enhances a flux rate of a substance into the biological membrane by a technique selected from the group consisting of iontophoresis, electroporation, electro-osmosis, sonophoresis, and pressurization.

The microporation device could comprise a disposable component or the microporation device could be for a single use after which the microporation device could be discarded. The disposable component could be treated with reagents which react with a biological fluid withdrawn from the biological membrane to produce a signal or measurable change in properties which could be predictably related to the quantity of an analyte within the biological fluid. The disposable component could be treated with one or any combination thereof of surfactants, hydrophilic or hydrophobic compounds. The disposable component could be treated with antimicrobial or anticoagulent or protease inhibitor compounds. The disposable component could comprise stimuliresponsive polar gel sections comprising a material that could be released by a thermal, chemical or electrical stimulus. The disposable component could comprise a material that releases a compound when heated.

The-microporation device could comprise a mixer located on or within the substrate, the mixer being capable of mixing a substance prior to transdermal delivery of a substance into the biological membrane. The microporation device could comprise a closed-loop delivery and monitoring system, wherein the closed-loop delivery and monitoring system is capable of modulating transdermal delivery of a substance through a biological membrane based on a value of a property of an animal.

Another embodiment of this invention is a method of manufacturing a microporation device, comprising obtaining a substrate and forming a conductive network on the substrate, wherein the conductive network provides electrical connections to a microporator. The method could comprise bonding an adhesive layer over the conductive network. The method could comprise forming a non-conductive plug on the perforations. The method could comprise bonding the conductive network to a reservoir.

Another embodiment is a method for forming openings in a biological membrane, comprising placing a microporation device in close proximity of the biological membrane and triggering the microporation device to form at least one opening in the biological membrane, the microporation device comprising at least one reservoir and a tissue interface comprising at least one microporator and a substrate, wherein the microporator is located on or within the substrate. The triggering could transfer heat to the biological membrane. The opening could have a diameter of 1-1,000 microns. The opening or artificial pore could be formed by a method selected from the group consisting of local heating, mechanical puncture, sonic energy, hydraulic puncture, and electroporation. The method could comprise anyone or more of the following: (a) applying an enhancer to the opening; (b) applying a permeant to the opening; (c) collecting a fluid from the opening; (d) monitoring an analyte in the fluid; (e) delivering a substance into the biological membrane; (f) mixing a substance prior to delivery of a substance into the biological membrane; and (g) delivering a substance into the biological membrane and collecting a fluid from the biological membrane.

An object of this invention is a method for administering a compound through a biological membrane to an underlying tissue matrix or obtaining a biological fluid sample from a tissue matrix under a biological membrane, comprising a) contacting a flux enhancement cell with a biological membrane, b) forming a seal between the outer wall and the membrane, wherein the reservoir outlet is in communication with an artificial pore in the membrane; c) applying positive pressure to the inner cavity of the reservoir; d) biasing the reservoir towards the membrane, thereby producing the compressed state of the membrane; e) biasing the reservoir away from the membrane, thereby producing the relieved state; and f) the biological membrane having an inner surface in intimate contact with the tissue matrix and an outer surface, thereby producing the relieved state, wherein the biological membrane has a resting state, a pressurized state in which the outer surface of the membrane is depressed to a substantially concave form relative to the resting state and the underlying tissue matrix is compressed, and a relieved state, wherein the outer surface of the membrane is biased into a substantially convex shape and the underlying tissue matrix is subjected to reduced pressure, and ii) wherein the flux enhancement cell comprises an outer wall, the outer wall defining a cell cavity, and a reservoir movably contained therein, the reservoir comprising an inner cavity and an outlet; the inner cavity containing a permeant. One embodiment of the method for administering a compound through a biological membrane to an underlying tissue matrix or obtaining a biological fluid sample from a tissue matrix underlying a biological membrane, comprises g) biasing the reservoir towards the membrane, thereby producing the compressed state of the membrane; h) biasing the reservoir away from the membrane.

Another object of this invention is a flux enhancement device comprising an outer wall, the outer wall defining a cell cavity; and a reservoir comprising an inner cavity and an outlet, wherein the reservoir is movably contained within the cell cavity. The reservoir could be movably linked to the outer wall with a compliant membrane. The flux enhancement device could comprise a microporator. The microporation device or flux enhancement device could comprise a closed-loop delivery and monitoring system, wherein the closed-loop delivery and monitoring system is capable of transdermal delivery of a substance through a biological membrane and withdrawal of an analyte transdermally through the biological membrane. The flux enhancement device could comprise could comprise a closed-loop delivery and monitoring system, wherein the closed-loop delivery and monitoring system is capable of modulating transdermal delivery of a substance through a biological membrane based on a value of a property of an animal.

FIG. 1 shows the general configuration of a TFTI (1) with plurality of poration elements (2). The microporators of a TFTI device are heated probe elements capable of conductively delivering thermal energy via direct contact to a biological membrane to cause the ablation of some portion of the membrane deep enough to form micropores. In FIG. 1, the poration elements (2) are resistive elements.

The resistive elements could take almost any shape, but are typically high aspect ratio, straight cylinders or bars with diameters or square cross-sections that range from 1 micron to 150 microns and lengths from 100 microns to 3000 microns respectively. When an electrical current pulse is applied to each element, the pulsed element could be controllably and rapidly brought to a specified high temperature, ranging from 120° C. to greater than 3000° C. (the upper limit is really set by the melting point of the material comprising the resistive element, for most tungsten alloys this is in excess of 3000° C.), whereupon this thermal energy could then be delivered to the contacting tissue to effect the thermal poration of the tissue.

The patterned array of resistive elements is connected to a conductive network that passes electrical energy to each of the resistive elements. The array of resistive elements are connected to the current pulse source either individually, as a series electrical system, parallel electrical system or some combination thereof. The instantaneous current required for the operation of the TFTIs depends mainly on the number of resistive elements in a device, parallel or series network configuration and size of the resistive elements. Instantaneous current flowing through the resistive element network could range from 1 milliamps to 40 amps, however, as the pulse duration is typically only a few milliseconds long, and the impedance of each element is quite low (in practice the typical resistance of a single tungsten alloy poration element has been measured to be less than 0.1 ohms) the average power requirements are quite modest. For example, in the extreme case of a 40 amp current pulse of 1 millisecond duration applied to the 0.1 ohm element, the total power delivered is:

$P$=Watt×seconds $P=1^2 R/1000=(40\times40)\times(0.1)\times(0.001)$, or $P$=160 milliwatts per poration element.

More common values of power consumption based on the practical parameters (1 amp peak current, 1 millisecond pulse duration, 0.05 ohm poration element impedance) used in the preferred embodiments of the invention are:

$P=1^2(0.05)(0.001)$=50 microwatts per poration element.

With a power requirement of only 50 microwatts per poration element, for a typical delivery patch which utilizes 100 individual poration elements the total power requirement to perform the thermal poration process is still only 5 milliwatts, power levels easily delivered from very small, low cost batteries.

The resistive elements are arranged in a two-dimensional pattern that is transferred directly to the surface of a biological membrane. The type of pattern produced is dependent on the application. For example a set of micropores designed to deliver a local anesthetic to an IV insertion site may have a narrow pore pattern beginning at the needle insertion site and extending along the expected path of the needle. The desired pore depth is also dependent on the application. Using the example above, the pore depths formed maybe designed to be relatively shallow at the needle insertion site and deeper along the needles path within the body.

Figure 2:
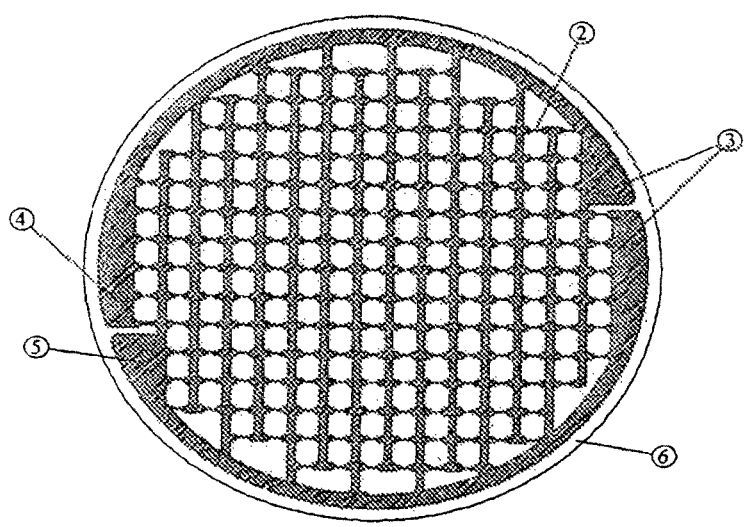
FIG. 2 shows an example of parallel conductive network and resistive elements.

FIG. 2 shows one embodiment of a parallel conductive network (3) with anode side (4), cathode side (5), poration elements (2) and supporting substrate (6). Each TFTI could be connected to an external electronic control module to supply electrical energy with the required current and pulse duration parameters.

The mechanism that forms a micropore is a result of the intimate contact of the biological membrane with the resistively heated element. In its most simple form, the TFTI would have resistive elements that stayed in contact with the skin before, during and after the poration process without moving. This would be known as a non-actuated poration process where resistive elements remain passively in the same location within the apparatus. The devices using micro-actuation combined with the resistive elements would be known as actuated microporation or actuation of poration elements.

The mechanism that forms a micropore is a result of the intimate contact of the biological membrane with the resistively heated element. In its most simple form, the TFTI of FIG. 2 would have resistive elements that stayed in contact with the skin before during and after the poration process without moving. This is known as a non-actuated poration process where resistive elements remain passively in the same location within the apparatus.

Another embodiment of this invention uses micro-actuation combined with the resistive elements and is known as actuated thermal microporation or actuation of poration elements. Micro-actuators produce a mechanical actuation of the poration elements and achieve greater control over pore depth, act to remove the resistive element from the micropore once it has been formed or perform a function such as opening a barrier that isolates a reservoir. An illustrative embodiment of an actuated microporator is shown in FIG. 3, which shows a wire resistive element in the unheated position (7) and the heated position (8).

Figure 3:
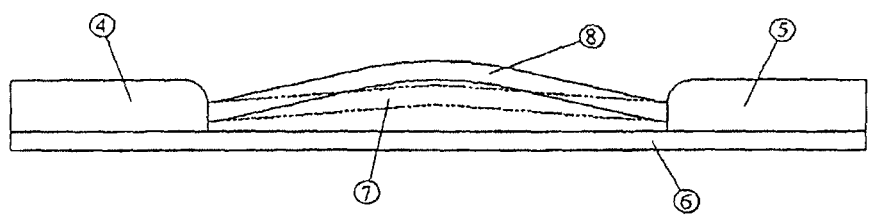
FIG. 3 illustrates the operation of a simple wire element actuator.
Figure 4:
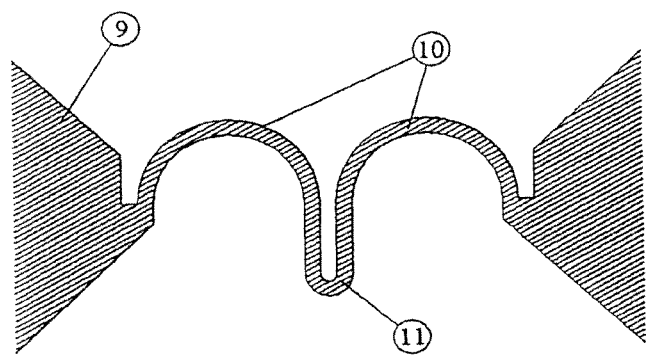
FIG. 4 shows a machined element actuator.

The actuated microporator of FIG. 3 is a straight tungsten wire element. FIG. 3 shows that the straight tungsten wire element undergoes a significant increase in length from position (7) to position (8) during the heating pulse as a result of the wires coefficient of thermal expansion as it undergoes the dramatic change in temperature of a typical thermal poration cycle. The anode side (4) and the cathode side (5) of the wire element are immobile and the wire reacts to the heating pulse by bending outward to accommodate its thermally induced increased length, away from the original centerline of the element. The direction of the wire motion could be designed to be directed away from the substrate (6) by forming a small initial bend in the poration element when in the unheated position. With this embodiment of an actuated TFTI device, micropores could be created without requiring an initial intimate contact between the biological membrane and the poration element. That is, when the poration element is heated and subsequently is actuated to move towards the biological tissue surface, the necessary contact between the poration element and the biological surface could be ensured by designing the geometries of the system and the amount of actuation travel to guarantee the required physical contact. The choice of wire element length, initial bend and wire temperature could be used to control the resulting pore depth in the biological membrane as well. Also, by knowing the actuation response as it relates to temperature, and by also knowing the change in impedance of the resistive poration element as it relates to temperature, one could monitor dynamically, both the temperature of the poration element and the resulting amount of actuation. Similarly, once contact is established with the targeted biological membrane, a detectable shift in the relationship between the amount of energy delivered to the poration element and the change in heat would occur, adding yet another level of dynamically measurable parameters to the poration process which could be used to help ensure the formation of controllably, repeatable pores at each poration element. By using these measurable parameters as feedback inputs to the controller, current source, the variance in individual poration elements which may result from the tolerances of the manufacturing process, could also be accommodated, allowing for additional cost savings in the manufacturing processes of the TFTI by being able to accept looser tolerances;

Another embodiment of an actuated microporator of this invention is shown in FIG. 4, wherein the actuated element is formed from a thin sheet of element material (9) such as tungsten or copper. Some of the element material is removed using a process such as laser micromachining to produce the resistive element shown in FIG. 4. During the laser micromachining process, it is possible to dynamically monitor the impedance of each poration element as it is formed. By using this sort of dynamically monitored fabrication process, a parallel or series array of poration elements could be formed where it could be ensured that the current pulse delivered is distributed in a balanced, uniform manner to each individual element. The shape of this resistive element was chosen to produce motion in the direction perpendicular to the plane of the sheet material during heating. The physical expansion of the curved sections (10) of the structure force the tip (11) of the element to lift away from the plane of the sheet material. Since the entire element reaches a high temperature, the tip (11) ablates tissue as it is forced into the biological membrane. The resulting pore depth in this case is controlled by the arc length of the curved sections (10), length of the tip region (11) and element temperature.

To additionally ensure the equal distribution of a current pulse to each poration element in an array, the specific thermal coefficient of resistance for the resistive poration element could be selected or designed such that as the individual element heats up, its resistance increases, thereby causing less current to flow in that specific poration element within a parallel network and at the same time forcing more current to go to the other poration elements in this same network. By using this natural phenomenon a self-balancing parallel network of resistive elements could more easily be designed and manufactured. This is similar to how a standard parallel wiring of a home lighting system operates when several incandescent lamps are connected on the same circuit.

In another embodiment of this invention, shape memory alloy (SMA) materials are used for the body of the resistive element. The use of SMA materials has the potential to maximize the efficiency and effectiveness of actuated poration.

A wide variety of micro-actuators could be used for the purpose of actuated poration. Manufacturing methods that employ more advanced processes such as photolithography are capable of producing more complex micro-actuators. Some micro-electromechanical systems that could be incorporated into TFTI devices include but are not limited to electro-static microactuators, thermal bimorph microactuators, piezoelectric microactuators, electromagnetic microactuators and SMA microactuators.

A preferred embodiment of the present inventive subject matter is a transdermal drug delivery device for forming a micropore in a tissue membrane of an animal. The transdermal delivery devices comprising a tissue interface layer having a substrate and at least one porator located on or within said substrate, at least one reservoir in communication with the tissue interface layer, and a controller for controlling the formation of the micropore by the porator. The porator is constructed of a heat resistive element which deforms when heated, thereby allowing the heat resistive element to contact the tissue membrane and form the micropore by ablating the tissue membrane. A permeant or analyte is stored within the reservoir. The substrate is selected from the group consisting of a woven material, a film, a supporting layer and a sheet. In a preferred embodiment, the controller applies a stimulus to the porator for forming the pore by deforming the heat resistive element. Further, the porator is selected from the group consisting of a wire conductor, a machined conductive material, a laser cut conductive material, an adhesive foil, an electroplated material, a shape memory alloy material and an etched conductive material. The device may further comprise an adhesive layer to bind the device to the tissue membrane.

The present inventive subject matter is also drawn to a method of using such a transdermal drug delivery device. In particular, the present inventive subject matter contemplates a method of forming at least one micropore in a tissue membrane of an animal. The method comprises the steps of: a) providing a poration device; b) contacting said poration device with the tissue membrane; c) providing a stimulus to at least one porator by way of a controller, thereby heating the at least one porator and increasing the length of and deforming same, causing the at least one porator to come into contact with the tissue membrane; d) forming at least one micropore; and e) cooling the porator, thereby decreasing the length of same and returning same to its original shape, resulting in the porator no longer contacting the tissue membrane. The poration device includes a tissue interface layer, at least one reservoir in communication with the tissue interface layer; and a controller for controlling the formation of said micropore by said at least one porator. The tissue interface layer comprises a substrate and at least one porator. The porator is located on or within the substrate and is constructed of a heat resistive element which deforms when heated. The substrate may be selected from the group consisting of a woven material, a film, a supporting layer and a sheet. The porator may be selected from the group consisting of a wire conductor, a machined conductive material, a laser cut conductive material, an adhesive foil, an electroplated material, a shape memory alloy material and an etched conductive material. The method may also include the step of applying a permeant composition stored in the reservoir to the micropore, or extracting an analyte by way of the micropore and storing the analyte in the reservoir.

Fusible TFTI designs are an alternative to actuated and non-actuated poration schemes. In the case of a fusible design, enough electrical energy is passed through the resistive element to destroy the element, taking it out of the electrical circuit. This also provides a mechanism of removing the element from the pore site. This embodiment of the invention also has the potential to greatly simplify the supporting electronics requirements. In the case of resistive elements that do not fuse or break their connection, the driving electronics are required to generate a signal of controlled duration and amplitude for sensation management. In the case of fusible elements, the thermal pulse duration could be controlled mainly by the physical failure properties of the element and the electronics are only required to deliver an impulsive signal with uncontrolled duration, as in the case of a capacitor discharging. Whereas simply delivering enough energy to the poration element to cause the conductive trace to melt or vaporize is one method of 'blowing the fuse', a more preferable method may be to fabricate the substrate holding the element out of a material which has been specified to undergo a thermal shrinking or tearing process when exposed to the elevation of temperature due to the activation of the poration element. With suitable attachment of the poration element trace to this tear-able substrate, when the substrate tears, it would also rip the element apart and thereby break the current path while simultaneously opening a path into a reservoir adjacent to the poration element. If this now connected reservoir contained a permeant for delivery, this permeant would now be disposed directly onto the just formed micropore in the biological membrane. By appropriately selecting the material for this tear-able substrate, this process could be made to occur at much lower, and more biocompatible temperatures, than what might be required if one were to simply 'blow the fuse'. Some materials that have this type of desired thermal properties are the heat-shrinkable polymers and vinyls commonly used in electrical insulation. To help ensure that the tear or rip occurs when and where desired, and at the designated temperature, this substrate could be formed with a small etch line, embossed stress point, or other such feature to provide the 'flaw' from which the thermally induce tear would originate. Another significant advantage of this type of thermally induced tearing is that the opening of the pore into a drug or assay containing reservoir could be produced with only a minimal amount of temperature for a very short period of time, minimizing the amount of thermal energy and peak temperature being presented to the reservoir. This feature is of particular importance when the reservoir contains thermally fragile peptides, proteins, assay enzymes or other drugs sensitive to thermal stress.

An embodiment of the present inventive subject matter is directed to a transdermal drug delivery device for forming a micropore in a tissue membrane of an animal, comprising a tissue interface, at least one reservoir in communication with the tissue interface layer, and a controller for controlling formation of the micropore by the porator. The tissue interface layer further comprises a substrate and at least one porator, wherein the porator is located on or within the substrate and the porator is constructed of a material in which the porator is destroyed upon forming the micropore. A permeant or an analyte may be stored within the reservoir. In a preferred embodiment, the controller applies a stimulus to the porator, and the stimulus initiates formation of the pore by the porator and then destroying the porator following formation of the micropore. The stimulus may be a thermal pulse or an electrical pulse.

A further embodiment of the present inventive subject matter is drawn to a method of forming at least one micropore in a tissue membrane of an animal. The method comprises the steps of: a) providing a poration device; b) contacting the poration device with the tissue membrane; c) providing a thermal or electrical pulse to the porator in the poration device by way of a controller, thereby forming the micropore in the tissue membrane; and, d) destroying the porator after forming the one micropore by sustaining the thermal or electrical pulse for a duration sufficient to destroy the porator. The poration device includes a tissue interface layer comprising, at least one reservoir in communication with the tissue interface layer; and a controller for controlling the formation of the micropore by the porator. The tissue interface layer further comprises a substrate and at least one porator, wherein the porator is located on or within the substrate and the porator is constructed of a material in which the porator is destroyed upon forming said micropore.

In another preferred embodiment of the device and methods, the substrate is constructed of a material which undergoes thermal shrinking when exposed to an elevated temperature due to activation of the porator, whereby the thermal shrinking results in a tear in the substrate and destruction of the porator. Suitable heat-shrinking materials have been previously discussed. In addition, the substrate may be formed with a flaw from which a tear would form.

The TFTI devices of this invention could also be enhanced by the addition of a range of substances at or near the poration element. This approach also has particular utility with elements that are fusible as previously described. The object of these substances is to produce a chemical reaction at the pore sites and during the poration process.

This chemical reaction could be tailored to perform a variety of functions. One example is coating an element with a pyrotechnic material or other material that results in an exothermic reaction. The energy used to ablate tissue would then come mainly from the exothermic reaction. This allows a simple way to reduce the electrical energy required to trigger poration and thus reduce the overall size of the integrated device. A second example is a combined exothermic and endothermic reaction. An initial exothermic reaction would produce a micropore and be followed closely by an endothermic reaction to cool the pore site and improve sensation experienced by patients.

A chemical reaction at the pore site could also be useful for the byproducts of the reaction. With appropriate choice of reactants, byproducts could perform all or some of the functions of flux enhancers, anti-clogging agents, permeants, therapeutic agents, reactants to drive subsequent reactions or other beneficial purposes.

The TFTIs comprising a resistive element could be manufactured by different methods. The first method uses a previously formed wire conductor to create the resistive element. By the second method, the resistive elements are created by a deposition of conductive material. By the third method, the resistive elements are formed by etching or machining of the element material. In addition, some manufacturing methods employ both deposition and etching. Several examples of TFTI manufacturing processes to demonstrate the manufacture of TFTI devices and illustrate the variety of manufacturing methods available as shown below. The invention is illustrated in the following non-limiting examples.

Example 1

A Woven Material TFTI Device

Some embodiments of the TFTI devices involve the use of previously manufactured wire conductors such as tungsten, tantalum, or tungsten alloy wire as the resistive element. There are a variety of methods for incorporating the wire conductors into a TFTI design. These methods include, but are not limited to weaving, sewing, bonding, brazing, spot welding, connecting with conductive adhesives or resins and laminating to a thin film or laminated structure.

Figure 5:
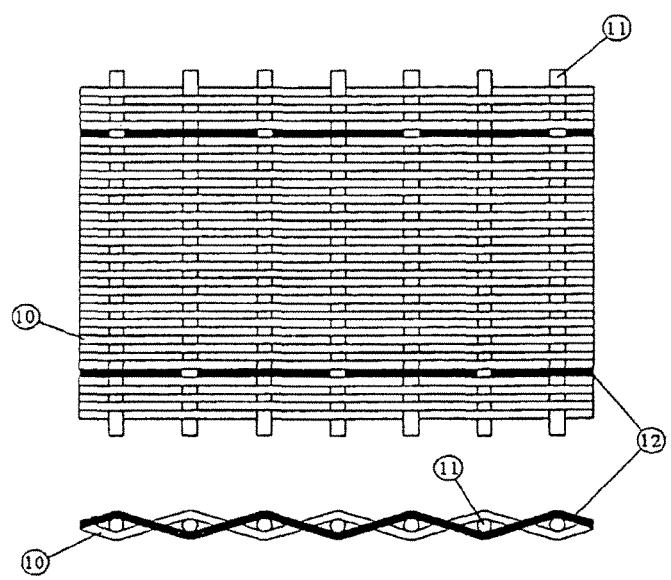
FIG. 5 is an enlargement of a hybrid woven material used as a basis for the manufacture of an example embodiment.

The basis of a woven material TFTI device is a hybrid woven fabric such as what is shown in FIG. 5. FIG. 5 is an enlargement of a section of the hybrid woven fabric and should be considered as extending outward in two dimensions as a repeating structure. The hybrid woven fabric contains a combination of structural fibers (10) and (11) which are not electrically conductive (such as polyester, fiberglass, nylon, mylar, polycarbonate, or the like) and electrically conductive fibers or strands (12) (such as tungsten or tantalum or copper wires, conductive polymers, glass or carbon fibers, or the like). In this example, polyester fibers of 50-micron (10) and 80 micron (11) diameters are woven with 50-micron diameter tungsten wire (12).

The electrically conductive fibers or strands are woven into the fabric and run in only one of the weave directions, spaced apart by a specific number of structural fibers depending on the desired poration element array density. Here the number of polyester fibers between two tungsten wires is 28 that would result in an element spacing of about 1.4 millimeters.

Figure 6:
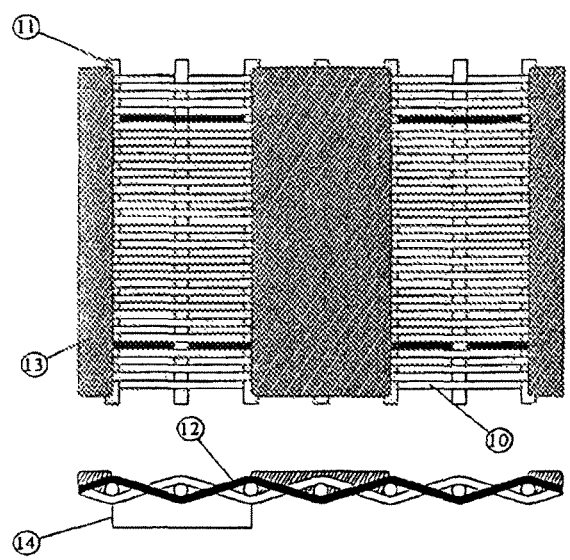
FIG. 6 is the same woven material shown in FIG. 5 with screen-printed conductive traces that form resistive elements along with the wire conductors.

The woven material is then processed to apply conductive traces on one side as shown in FIG. 6, creating the desired conductive network (13) with the interwoven conductive fibers forming the resistive elements (14). These traces may be created in a variety of ways including: pressure transfer of conductive/self adhesive foils onto this surface; electroplating into the desired pattern using either a shadow mask or resist mask to define the traces; or simply screen-printing with electrically conductive ink or resins and curing. Most conductive inks are designed to allow a certain amount of flexibility after curing which results in a more compliant TFTI device. For this example, the conductive network in FIG. 6 is arranged as a parallel electrical circuit although series or combined series and parallel configurations could be accommodated by this design. A silver impregnated epoxy is used to form the conductive network that is applied using standard screen-printing techniques.

An added advantage of the woven material TFTI devices is that proper choice of conductor thread count would result in resistive elements on both sides of the TFTI. This results in the optional use of the TFTI to breach or open a drug reservoir simultaneously with the creation of micropores. Areas of the fabric that are not covered by the conductive network would then be able to pass a deliverable substance from a drug reservoir, through the TFTI and into the micropores.

Once the application of the conductive network to the woven fabric has been completed, further integration of the TFTI could take place that may include bonding to a drug reservoir or addition of an adhesive layer to maintain contact between the TFTI and the biological membrane to be porated. This design is also conducive to the integration of other functional features that include iontophoretic electrodes, flux enhancer releasing elements, buffer releasing elements, analyte assay electrodes. The analyte assay process could also be accomplished via optical means by looking for a colorimetric shift in response to the selected analyte's concentration.

The present inventive subject matter is directed to a transdermal drug delivery device for forming a micropore in a tissue membrane of an animal. The transdermal drug delivery device comprises a tissue interface layer. The tissue interface layer further comprises a substrate comprising a woven fabric, with the woven fabric comprising structural fibers and electrically conductive fibers interwoven together as is discussed above. The tissue interface layer also comprises at least one porator, wherein the porator is located on or within the substrate and is formed by the electrically conductive fibers acting as a heat resistive element. The transdermal drug delivery device also includes at least one reservoir in communication with the tissue interface layer and a controller for controlling the formation of the micropore by the porator. The transdermal drug delivery device of the present embodiment may also have the electrically conductive fibers connected in parallel or series by conductive traces, thereby forming a conductive network. The conductive traces are selected from the group consisting of foils, inks, resins, electroplating products and mixtures thereof.

The present inventive subject matter is also directed to a method of manufacturing a transdermal drug delivery device in accordance with the details set forth above. The method comprises the steps of: weaving electrically conductive fibers into a fabric of non-electrically conductive fibers to form an electrically conductive fabric; applying conductive traces to one end of the electrically conductive fabric to form a conductive network; and connecting the conductive network with a controller which controls the application of electricity to the conductive network.

In another embodiment, the present inventive subject matter includes a method of forming at least one micropore in a tissue membrane of an animal. The method includes the steps of: providing a poration device, contacting the poration device with the tissue membrane and actuating the poration device to form the micropore in the tissue membrane. The poration device includes a tissue interface layer, at least one reservoir in communication with said tissue interface layer and a controller for controlling the formation of said micropore by said at least one porator. The tissue interface layer further includes a substrate comprising a woven fabric, said woven fabric comprising structural fibers and electrically conductive fibers interwoven together and at least one porator located on or within the substrate. The porator is formed by the electrically conductive fibers acting as a heat resistive element.

Example 2

A Wire Overlay TFTI Device

This TFTI design utilizes a unique screen-printing process that involves overlaying wires on a substrate and then printing conductive traces over the wires to both form electrical connections with the conductive network and bond the wires to the substrate. This example design also uses SMA wire as the resistive element material to produce an optimized actuation of the poration element. The poration elements are designed to alter their shape during the poration process and breach a drug reservoir directly over the pore site.

Figure 7:
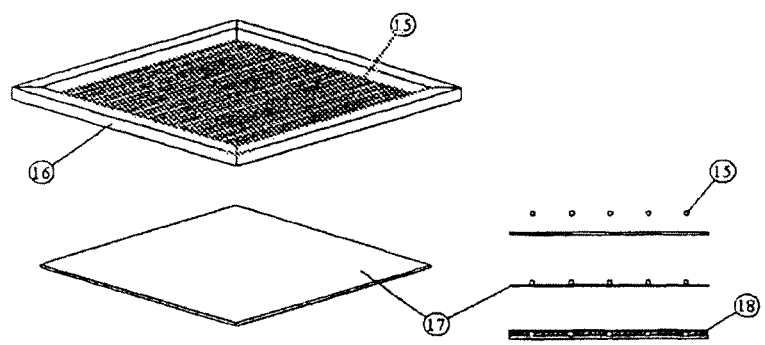
FIG. 7 illustrates a unique screen-printing technique used to manufacture an example embodiment.

As shown in FIG. 7, multiple lengths of SMA wire (15) such as nitinol are mounted in a frame (16) with a spacing given by the desired element density in the final array. A spacing of 1.00 mm between lengths of SMA wire is used. The frame and mounted wires are then placed over a thin film substrate (17) and standard screen-printing techniques are used to deposit conductive ink (18) onto the substrate and SMA wire combination to produce an electronic network. The SMA material chosen for this application should have a high melting point such as nitinol. The substrate material must be non-conductive and have a low melting point such as polyester. A good candidate conductive ink should have a high conductivity and be flexible after it is fully cured such as a silver/polymer conductive ink.

Figure 8:
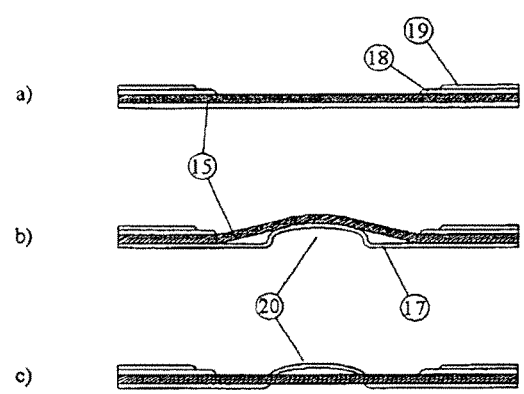
FIG. 8 is an enlarged side view of a single poration element in an example embodiment shown during manufacture, completed and after activation.

The next step in the manufacturing process is to emboss the array at each of the poration element locations. FIG. 8a shows an enlarged side view of a single poration element after the screen-printing process and before embossing occurs. A dielectric or adhesive layer (19) prevents the conductive ink network from making contact with the skin or other biological membrane.

FIG. 8b shows an element after it has been embossed. It is important that the embossing process does not cause the SMA material to anneal or undergo a change in crystal structure. This would allow the SMA material to return to its original shape (straight) when heated resistively by the conductive network as shown in FIG. 8c. As an element becomes heated, it initially creates a skin pore due to intimate contact with the surface of the skin. As further heating of the element occurs, the SMA material begins to return to its original shape and retract from the newly created pore while simultaneously forming an opening in the embossed feature (20) of the supporting substrate. This could then open a pathway between a reservoir on the opposite side of the substrate and the microscopic pore as described above. Some embodiments of the TFTI devices involve resistive elements that are deposited by processes such as electro-discharge machining (EDM), sputtering, screen-printing, electroplating and chemical vapor deposition (CVD) that are common to the flexible circuit and electronic industries. The following section illustrates a TFTI device that could be manufactured using any of the above deposition processes.

Example 3

A Sputter Deposited TFTI Device

Figure 9:
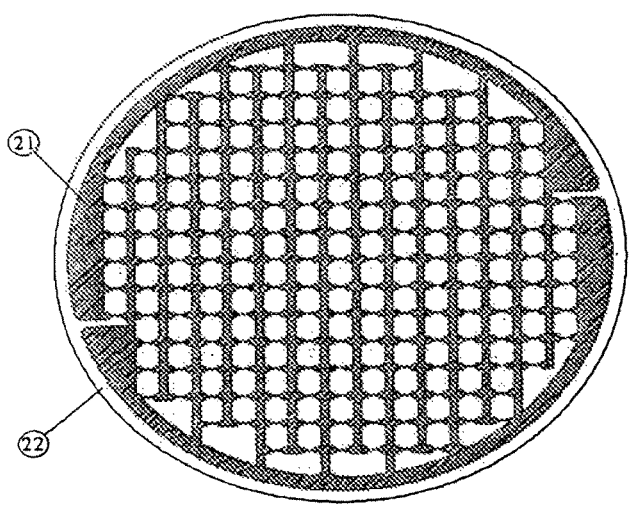
FIG. 9 is a tantalum, parallel conductive network and resistive elements deposited in an example embodiment.

The first step involved in manufacturing is the deposition of a material such as tantalum by sputtering to form the resistive elements and conductive network on an appropriate substrate such as 50-micron polyamide. FIG. 9 shows the pattern of deposited tantalum traces (21) on the polyamide substrate (22). A parallel electrical configuration is used for purposes of illustration, however the conductive network could be designed to address each poration element single or in a parallel circuit, series circuit or any combination of parallel and series circuits.

Figure 10:
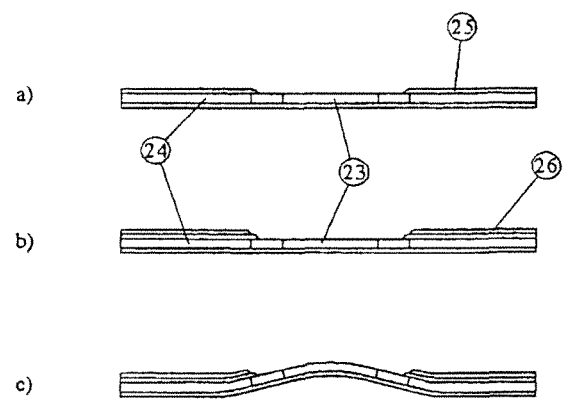
FIG. 10 is an enlarged side view of a single poration element in an example embodiment shown during manufacture and in its final form.

Depending on the properties of the material used for the conductive network and resistive elements, it may be desirable to deposit additional material onto the pattern everywhere except for the resistive elements themselves. The additional material could be any other type of compatible conductive material and serves the purpose of reducing the resistance of the conductive network and thus reducing the overall power required to operate the array of resistive elements, as well as confining more precisely in a spatial sense those areas of the TFTI which would undergo the cycling to the ablation temperature threshold. FIG. 10 shows an enlarged side view of a single resistive element (23) at different points in the manufacturing process with adjacent conductive network connections (24). FIG. 10a shows the element after the initial deposition and an optionally additional layer over the conductive network (25).

The next step in the manufacturing process is the placement, screening or bonding of an adhesive layer (26) over the conductive network without covering the resistive elements as shown in FIG. 10b. The purpose of the adhesive layer is to bond the biological membrane such as skin to the TFTI and ensure that there is intimate contact with the resistive elements. The final step in the manufacture of the TFTI is optionally embossing in the area of the resistive elements as shown in FIG. 10c. The purpose of embossing is to move the resistive element near or even proud of the adhesive, biological membrane contacting side of the TFTI and ensure intimate contact between the resistive element and the biological membrane to be microporated. The embossing process could also serve to thin the substrate material in the area of the resistive element. This may help the resistive element to breach the substrate material during poration, thus providing a mechanism by which a substance is introduced to the pore site for drug delivery applications. Another possible advantage of embossing for any TFTI design is that the resistive element material would undergo strain hardening and thus provide a method for altering the electrical and mechanical properties of the element. Additional flexibility in tailoring of properties is achieved by varying the temp of the material during the embossing process.

It should also be noted that many deposition techniques are conducive to the manufacture of complex resistive element geometry's for the purposes of actuated poration. Some techniques, commonly used in the mass-production of electronic components are capable of depositing structures with feature sizes of 0.5 microns or less.

Some embodiments of the TFTI devices involve resistive elements that are etched or machined from a layer or sheet of material by processes such as laser micromachining and a range of photolithography techniques common to experimental MEMS devices and the electronics industry. The following section illustrates a TFTI device that could be manufactured using a micromachining process.

Example 4

A Micromachined TFTI Device

Figure 11:
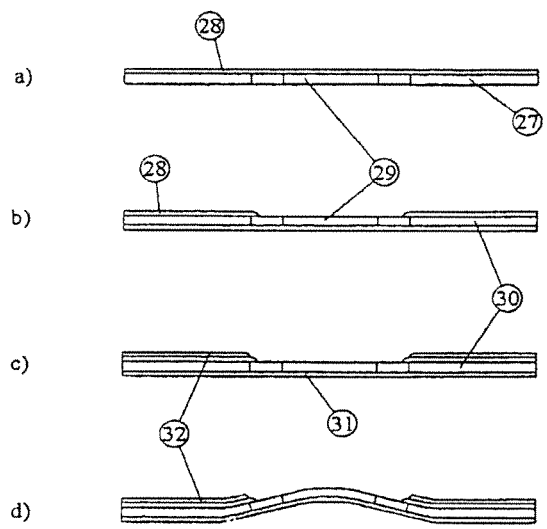
FIG. 11 is an enlarged side view of a single poration element in an example embodiment shown, during manufacture and in its final form.

FIG. 11 shows an enlarged side view of a single resistive element at different points in the manufacturing process. The first step in the manufacturing process is to laminate thin films of the resistive element material (27) such as tungsten in a 30 micron sheet to a supportive or resistance tailoring layer such as copper (28) in a 50 micron sheet. These layers are then micromachined using a laser from the tungsten side as shown in FIG. 11a. Laser power, repetition rate and cutting speed are adjusted so that the resistive elements (29) and conductive network (30) are produced without cutting through the supportive or resistive tailoring layer. Also, during this process of laser micromachining, the laser energy could be used to effectively form the electrical bonds between the tungsten poration elements and the resistance-tailoring layer.

The next step shown in FIG. 11b is to bond the tungsten side of the structure in FIG. 11a to a nonconductive layer such as polyester (31). This laminated structure is then laser micromachined from the copper side (28). At this point the copper is no longer needed as a structural support. The result of this process is to leave copper material on the conductive network only and remove it from other locations including over the resistive elements. Care is taken in the laser parameter settings to avoid cutting through the nonconductive layer (31). The next step in the process is to bond an adhesive layer (32) over the conductive network with the resulting structure shown in FIG. 11c. The final step in the manufacturing process is to emboss the nonconductive layer at the locations of the resistive elements as shown in FIG. 11d.

Example 5

A Simple Screened TFTI Device

Figure 12:
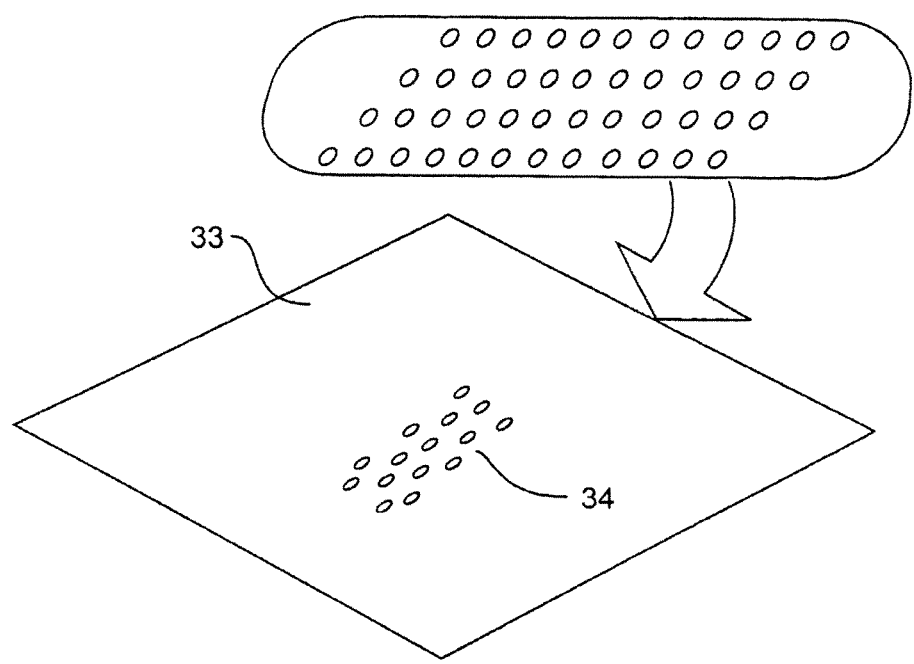
FIG. 12 shows a perforated polycarbonate sheet that is the basis for an example embodiment.
Figure 13:
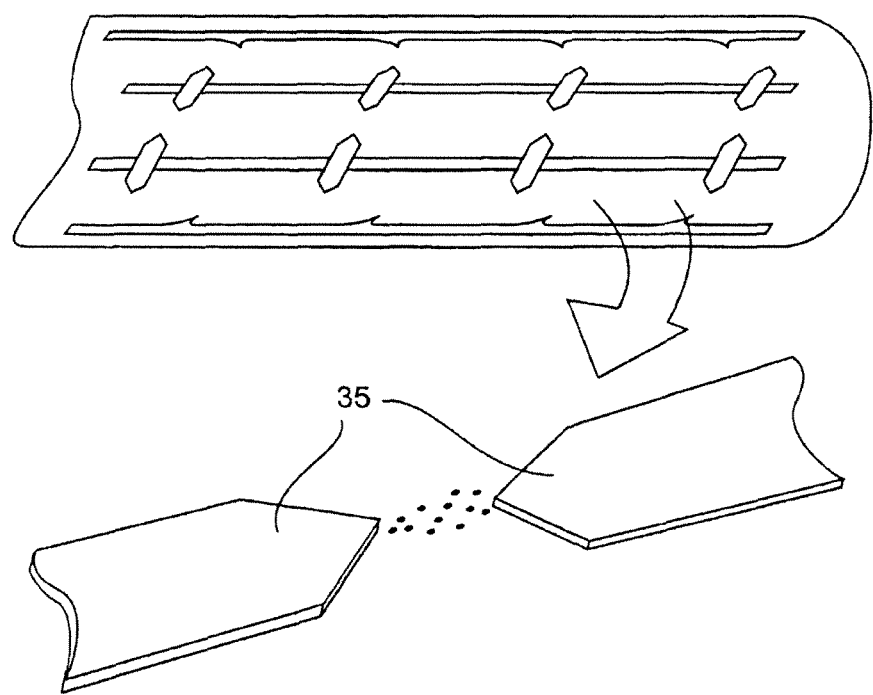
FIG. 13 shows the perforated sheet in FIG. 12 with screen-printed conductive traces.
Figure 14:
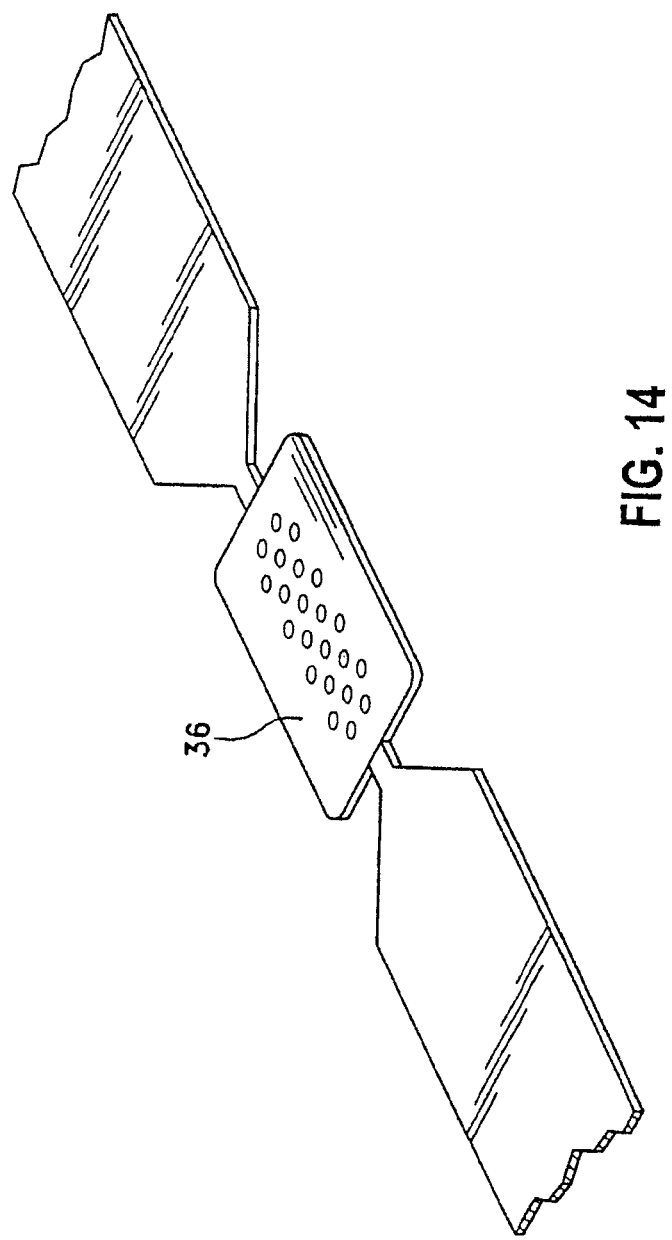
FIG. 14 shows the perforated sheet and conductive network of FIG. 13 with screen-printed plug material.
Figure 15:
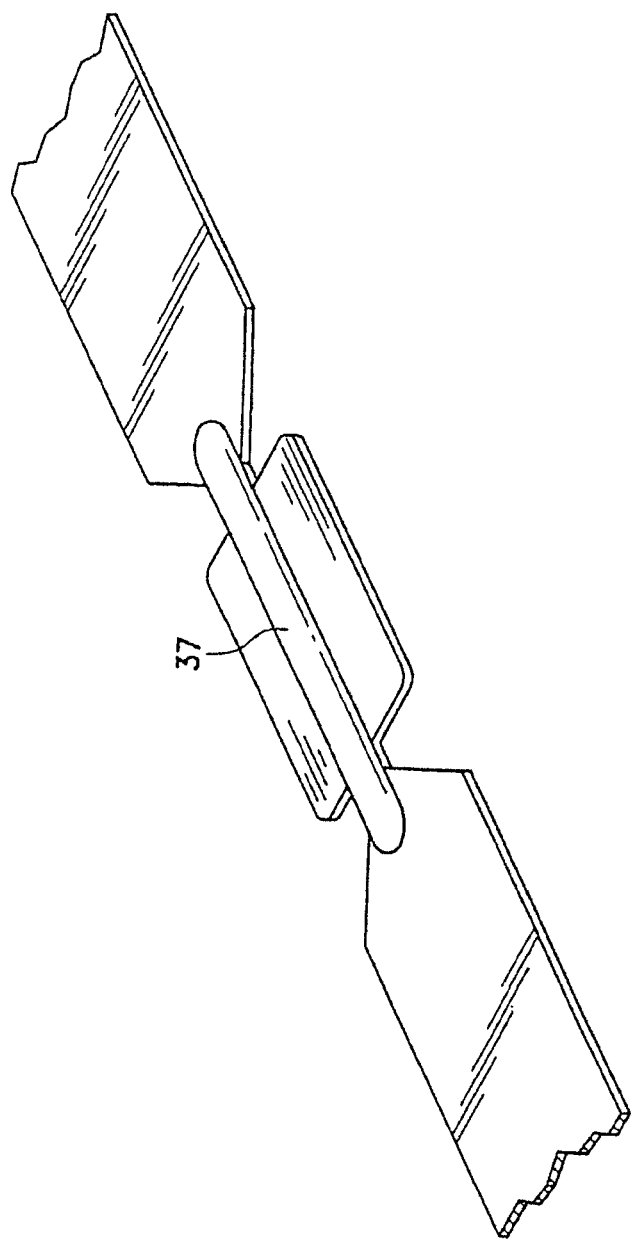
FIG. 15 shows the device of FIG. 14 with a screen-printed resistive element.
Figure 16:
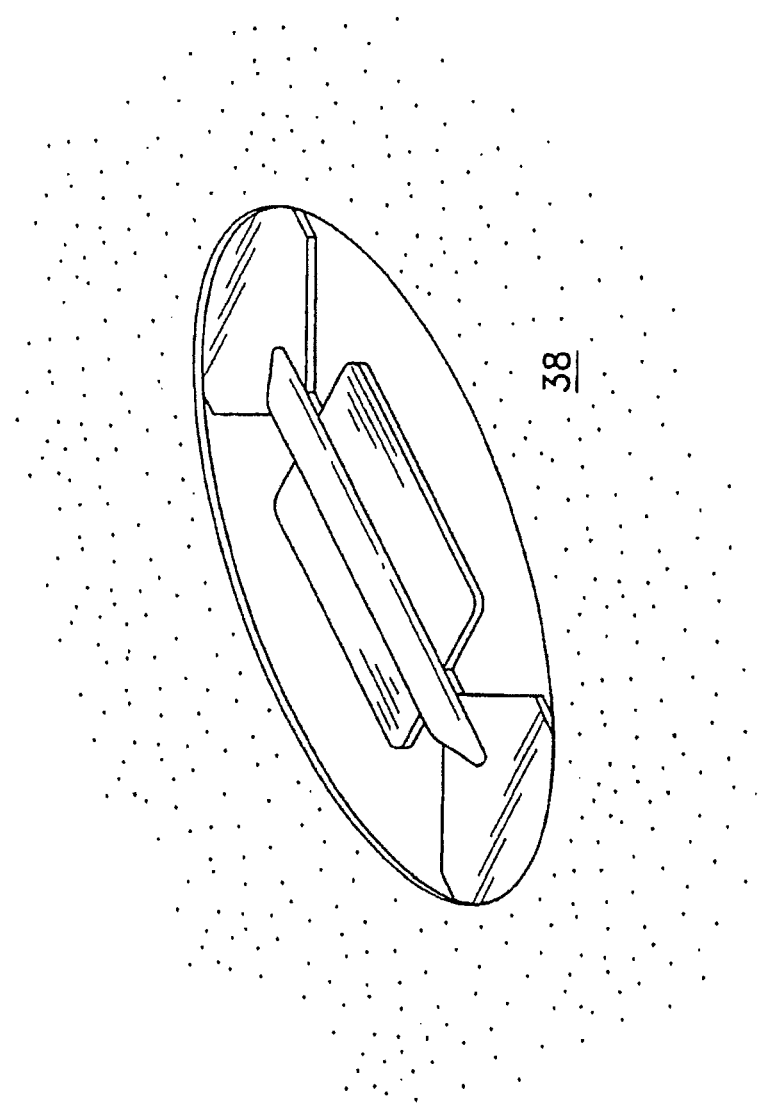
FIG. 16 shows the final form of an example embodiment with a screen-printed skin sealing adhesive layer.

The following example utilizes screen-printing almost entirely to form the TFTI device. A 20-micron thick polycarbonate sheet (33) is obtained and about 10-20 micron diameter perforations (34) are made in the sheet as shown in FIG. 12. The perforations (34) could be made by laser processing, mechanical punching or other method for perforating a sheet. The perforations could be of any shape ranging from 1 micron to several millimeters. The perforations are generated in tight groups, with multiple tight groups forming a larger array. The next step is to screen-print a conductive network (35) without elements onto the polycarbonate sheet as shown in FIG. 13. The conductive network may be formed using silver conductive ink in a flexible when cured carrier and allowed to cure. Next a low melting point, nonconductive plug material such as wax (36) is screened over the perforations to seal them as shown in FIG. 14. Then additional conductive ink (37) is screened to form a fine bridge of material connecting the two sides of the conductive network over each wax plug as shown in FIG. 15. This is the resistive element that becomes heated during the poration process. The conductive ink used to form the resistive poration element may be the same as that used to form the conductive network or it maybe selected to be or a different material, such as a carbon conductive ink, to be more suitable for this design purpose. This design functions by creating a micropore initially and then further heating removes the plug material by either a melting process or the thermal ripping or tearing process described previously and opens a pathway between the micropore and a reservoir. The final step in manufacturing the TFTI is to screen an adhesive (38) as shown in FIG. 16 to ensure intimate contact between each resistive element and the biological membrane to be porated and also to act as the principal attachment mechanism of the device to the subject's body.

Any of the TFTI designs discussed here could be designed to allow for individually addressable resistive elements. The addition of diodes to the conductive network would allow current directional isolation of individual array elements which supports some schemes by which individual elements could be activated with a 'row-column' addressing approach, similar to how an individual pixel might be toggled in a two dimensional visual array. An integrated device design that used separate reservoirs for each poration element could benefit from an individually addressable poration element control scheme. Another advantage of this approach is an overall reduction in the peak power required to activate the TFTIs. The maximum peak current required to effect poration would be smaller than that if single elements were activated one at a time. Also, by having each cell comprising a poration element, and its associated micro-reservoir being essentially individual, independently controlled systems, one could program the controller system to only activate a certain number of these cells at a time, allowing more control over a drug delivery profile or when the cells are used to effect the assay of an analyte, individual assays may be made at various selected points in time.

A feature of the TFTI designs of this invention is that manufacturing processes are used that allow the technology to be scaled down drastically. Techniques such as photolithography are able to produce TFTI designs with high densities of extremely small poration elements. Scaling down the size of poration elements has potential advantages such as reduced energy required for poration, improved skin surface healing and improved patient sensation.

The devices of this invention could be manufactured using micro-electromechanical systems (MEMS) manufacturing technology. The micromanufacturing technology is suitable for cost effective mass production. In other embodiments of the devices of this invention, there could be micromachines integral to and working with TFTI devices. For example, microactuators could be designed to deliver permeants by individual pore microinjectors. The microinjectors could be made integrally with the resistive element so that the microinjector body thermally ablated tissue, extended into the skin layer and delivered a short-duration, high pressure fluid injection on a microscopic level.

Another example of microsystem technology could be applied to TFTI designs is in the area of tattoo removal. An array of micromachines could be designed to progressively lift up microscopic flaps of skin and remove dye-bearing tissues. In fact a closed loop control scheme could be used where integrated microsensors detect the location of dye bearing tissues, a microprocessor then determines the best course of action.

The use of sensors and actuators in the same TFTI device allows the creation of extremely sophisticated and intelligent microsystems. A single TFTI device could be built that drew interstitial fluid from pore sites and assayed for a particular analyte (such as glucose) and also delivered a substance through other pores (such as insulin) based on the results of the analyte measurement.

Example 6

Integrated Tissue Poration and Drug Delivery Device

The microporation device of this invention could be used as an integrated device for the creation of small holes or perforations or micropores in tissue, the delivery of drugs or other permeants through the micropores, the extraction of biological fluids through the micropores, and the assaying of analytes in an extracted biological fluid or permeants to be delivered.

Figure 17:
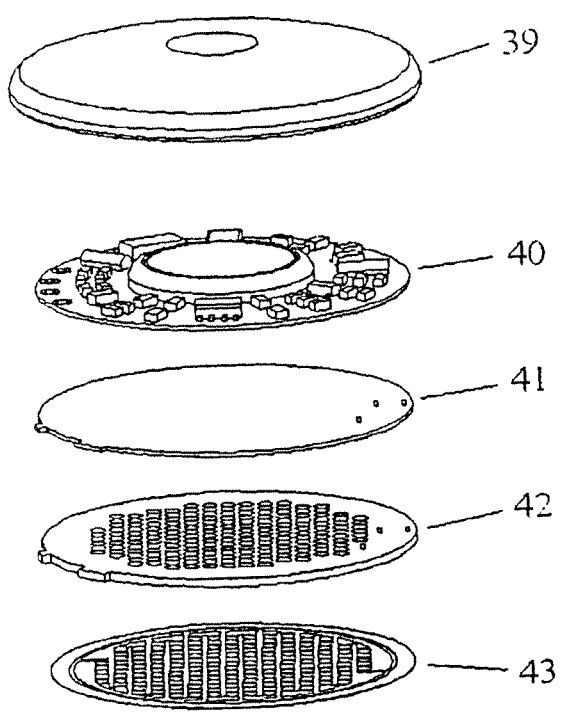
FIG. 17 is an exploded view of one embodiment of an integrated device.

The integrated device is a multi-component device comprising a tissue-interface layer comprising at least one microporator and at least one reservoir, one or more distinct reservoirs, a power supply, batteries, electronics, display and case. FIG. 17 shows one embodiment of a single or a multi-component device of this invention showing a thin cap (39) that forms the outer body of the device, a controller board (40) that contains driving electronics and a battery, a thin film top plate (41) and reservoir wall (42) that forms the top and sides of the chambers that contain the permeant for delivery. Finally a TFTI device (43) forms the bottom of the permeant chamber. In this design the top plate (41), reservoir wall (42) and TFTI device (43) are bonded together to form the disposable portion of the device containing the permeants for delivery. The disposable (41-43) and the controller board (40) are designed to fit completely into the thin cap (39) with the TFTI exposed on the bottom surface of the device.

One embodiment of the device is a single, disposable unit. An alternate embodiment has a subset of the components incorporated into a disposable portion while the remainder of the components is reusable. The device may be manufactured in more than one version, for example a personal version or a clinical version, with slightly different formats but similar functions. Some versions would be effective with fewer components and a reduced functionality. All versions would be discrete and small (on the order of one half (0.5) to ten (10) cubic inches).

A further embodiment includes an integrated device for forming a cavity in a surface of a tissue of an animal. The integrated device comprises a controller board connected to an energy source for actuating at least one porator, a fluid reservoir in fluid communication with the tissue; and a tissue interface layer, the tissue interface layer containing the at least one porator, the porator in contact with the tissue for forming the cavity. The reservoir and the tissue interface layer may be removably attached to the outer body. In a still further embodiment, the reservoir patch is separate from the integrated device and applied to the porated area of the tissue membrane following poration thereof.

If the case of a separate reservoir patch, the patch may comprise a top layer, a middle layer that has at least one cavity for containing a drug or other permeant composition to be applied to the membrane, and a bottom layer containing pores through which the drug is applied to the tissue membrane. The bottom layer may contain an adhesive for attachment of the reservoir patch to the microporated area of the tissue membrane.

Figure 18:
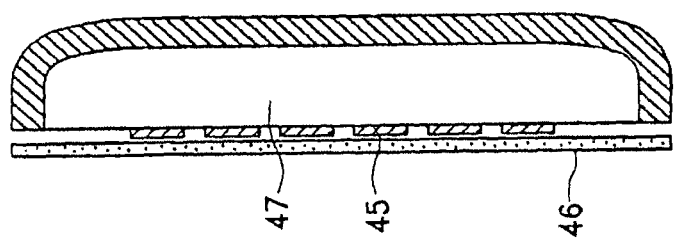
FIG. 18 shows one embodiment of the integrated device, with one permeant chamber and a tissue interface.
Figure 18:
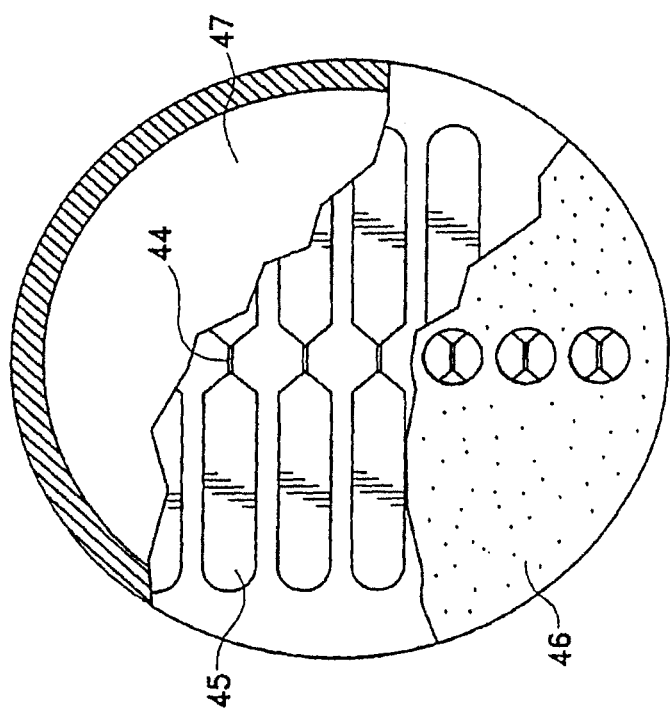

The tissue interface layer comprises some or all of the following: elements for effecting the poration of the tissue, adhesive for attaching the device to the tissue, reservoirs containing permeants for delivery, reservoirs for holding extracted biological fluids, and reagents fur assaying an analyte. The tissue interface layer could also include hydrophilic and hydrophobic surface treatments to act as fluid flow modifiers for controlling the motion of liquid permeants or biological fluids collected. The tissue interface layer may also incorporate antimicrobial agents to prevent sepsis or anticlotting or anticoagulents to control the aggregation of permeants or biological fluids extracted. The tissue interface layer may also be treated with permeation enhancers or buffers used for pH stabilization. The tissue interface layer may contain stimuli-responsive polymer gel sections, saturated with beneficial permeants, which could be triggered to release the beneficial permeants through a thermal, chemical or electrical stimulus. The tissue interface layer may release beneficial permeants on demand when heated, for example by the poration elements or other similar elements on the tissue interface layer. The tissue interface layer may contain piezoelectric elements for delivery of acoustic energy into the tissue or permeants being delivered or biological fluids being extracted. The tissue interface layer is intended to become part of a disposable as shown in FIGS. 18 and 20 or may be permanently mounted in the integrated device as in FIG. 19. FIG. 18 shows one embodiment of the integrated device showing the poration elements 44, conductive traces to the elements 45, the adhesive layer 46 with holes beneath the poration elements 44 and a single permeant reservoir 47.

Figures 19A, 19B, 19C:
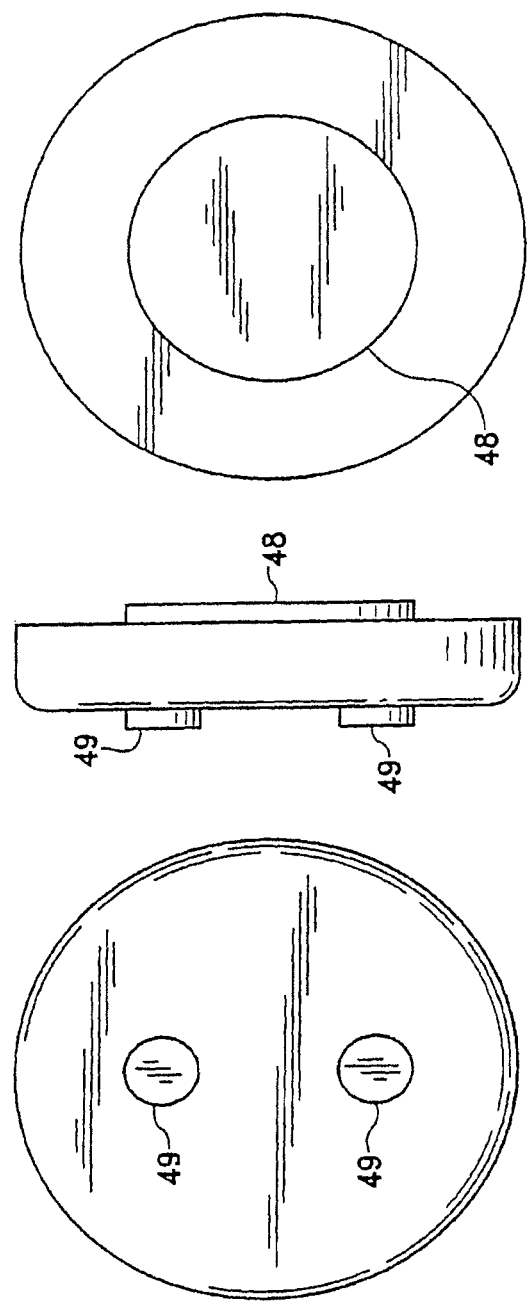
FIG. 19 shows one embodiment of a totally disposable integrated device.

FIG. 19 shows one embodiment of the integrated device where the entire device is disposable. In this embodiment, intended for single use, the poration elements, adhesive layer and permeant reservoir (all represented as 48) are permanently installed in the device. This embodiment has two control buttons 49 on the upper surface of the case. Pressing one button would initiate the poration process and basal delivery of the permeant. Pressing the other button would deliver an additional preset amount of permeant.

FIG. 20 shows an embodiment of the integrated device having a reusable component 50 and a disposable component 51. The reusable component 50 contains a permeant reservoir 53 and a skin interface 52. Batteries and circuits are housed in the reusable component 50. After a single use, the disposable component 51 would be replaced, thereby replenishing the permeant, the poration elements, and the adhesive which are all parts of the skin interface 52.

In addition to the poration elements, other conductive traces, or wires may be, incorporated into the tissue interface layer to act as all or some of the electrodes for electroporation iontophoretically enhanced delivery of a permeant into the tissue or for the enhancement of the extraction of biological fluids from the tissue for the purpose of monitoring one or more analytes. These electrodes may also be used to provide all or part of the current path via which one may deliver pulses of electrical energy into the tissue for the purpose of electroporating selected tissues within the current path. These electrodes may also be used for sensing through a drop in impedance that poration has occurred. Electrically conductive poration elements themselves could be used as one of the electrodes for either iontophoresis, or electroporation, or impedance sensing.

The tissue interface layer may comprise one or more reservoirs. In the case of multiple reservoirs, these reservoirs could be used to keep different and perhaps incompatible permeants separate. Delivery of permeants from the reservoirs could be simultaneously or sequentially. A reservoir wall is typically "porated" to breach the reservoir membrane and allow the delivery of the permeant into the tissue. This poration of the reservoir is accomplished with the same type of poration elements as are used to porate the tissue. Prior to the breach of this reservoir, the reservoir could maintain a stable, sealed, and sterile environment for the permeant, allowing the entire disposable portion of the integrated device to be manufactured and packaged efficiently and economically. The breaching of the reservoir may occur before, coincidentally with or after the poration of the tissue as required. Additionally, the flux rate of a permeant from a particular reservoir into the tissue is proportional to the area of the micropore coupling the reservoir to the biological membrane, if all other factors such as micropore density or iontophoretic current are the same. A reservoir could initially be empty or contain an absorbent material, in order to serve as a storage location for extracted biological fluids. Reagents for the assay of an analyte in the biological fluid would typically be located at the entrance to the extracted biological fluid storage reservoir.

The electronics for controlling the device are responsible for initiating the poration process, controlling the timing and amounts of permeants delivered, enforcing limits on the delivery mechanisms, processing the data for analyte assay and environment sensing, control of piezoelectric elements, and control of the user interface display if any.

Environment sensing could include temperature, humidity, and pressure. These values, particularly the temperature, could affect the results of assays performed by the device. Battery requirements for electroporation, and iontophoresis are minimal due to the large drop in resistance that typically occurs when the tissue is porated. Batteries of the flat, coin cell variety are sufficient. Nevertheless, in a clinical environment where the reusable component of the integrated device is used frequently, an external power source could be used. Some embodiments require or are facilitated by providing information to the user. In these embodiments, a display is provided on the top of the case.

Example 6A

Passive Vaccine Delivery Device

This embodiment of the device would be used in a clinical setting, where a patient receives a disposable patch that delivers the vaccine by diffusion through the micropores over a number of hours or days. The disposable for this embodiment would be simple, small, thin and inexpensive. The disposable would consist of a thin sealed reservoir with thermal poration elements and adhesive on the bottom and electrical contact pads on the top. The contact pads are attached to traces that lead to the thermal poration elements. The reservoir contains the vaccine to be delivered. The disposable is inserted into the reusable component of the device in a clinical setting. The entire device is placed against the surface of the skin so that the adhesive fixes the disposable to the surface of the skin. The thermal poration elements are activated, porating the surface of the skin and simultaneously breaching the lower surface of the reservoir allowing the vaccine to flow down and into the micropores, The reusable component of the device is then removed from the disposable portion, leaving the disposable portion attached to the surface of the skin and precisely registered to the micropores, allowing the vaccine to passively diffuse into the skin until the disposable is removed and discarded. This method for delivering a vaccine antigen has particular advantages in that the portion of the autoimmune system optimally targeted by an antigen to induce the best antibody response is the langerhans cells or dendritic cells. These langerhans cells or dendritic cells exist within the epidermis, exactly those tissues to which this method of delivery places the permeant being delivered.

Example 6B

On-Demand Pain Medication Delivery

This embodiment of the device is entirely disposable. The device comprises a reservoir for hydromorphone or other suitable opiate, circuitry required to support the thermal poration process, circuitry required to support the iontophoretic delivery of the hydromorphone, adhesive for attaching the device to the surface of the skin, thermal poration elements, a button to initiate delivery and a button for breakthrough pain dosing. The device has at least one counter electrode pad that contacts the skin while the device is used. The poration elements are used as the delivery electrodes after the poration step. The device is placed against the surface of the skin so that the adhesive fixes the device to the surface of the skin. The initiation button is pressed, activating the thermal poration elements, porating the surface of the skin and simultaneously breaching the lower surface of the reservoir allowing the hydromorphone to flow down and into the micropores. Iontophoretic delivery of the hydromorphone at a basal delivery rate commences. For breakthrough pain, the patient presses the other button on the surface of the device that temporarily increases the iontophoretic current to deliver a burst of hydromorphone. After many hours or days, the entire device is removed and discarded.

Example 6C

Use of Multiple Reservoirs

This embodiment of the integrated device comprises a reservoir for a drug, another reservoir for a capillary permeability enhancer such as $NH_3$, and another reservoir for a pH-neutralizing compound. The device includes thermal poration elements, circuitry required to support the thermal poration of the tissue, circuitry required to support the thermal poration or breaching of the reservoir walls, circuitry required to support the iontophoretic delivery of the permeants, and adhesive for attaching the device to the surface of the skin. The device has at least one counter-electrode pad which contacts the skin while the device is being used. The poration elements are used as the delivery electrodes after the poration step. The device is placed against the surface of the skin so that the adhesive fixes the device to the surface of the skin. The thermal poration elements are activated, porating the surface of the skin and simultaneously breaching the lower surface of the reservoir containing the $NH_3$. Additional poration elements are used to heat the $NH_3$ reservoir, creating gaseous $NH_3$ and water. After a short wait, the drug reservoir is breached and the drug is iontophoretically delivered. An iontophoretic current slowly alters the pH of the tissue, possibly interfering with further iontophoretic delivery as well as irritating the tissue, so after a period of minutes the pH neutralizing reservoir is breached and some pH neutralizer is delivered into the tissue to bring the pore interface zone hack to near physiological pH of 7.2. Alternate delivery of drug and pH neutralizer continues as necessary to delivery the desired amount of drug.

Example 7

Pressure Modulation and Flux Enhancer

The microporation device of this invention could be used as an integrated device in conjunction with a pressure modulation and flux enhancer. However, the pressure modulation and flux enhancer could be used as a stand-alone device or in conjunction with any other device, preferably medical devices.

The pressure modulation and flux enhancer of this invention utilizes pressure modulation to increase transmembrane flux through one or more micropores in the membrane. Forced compressions followed by forced expansions of the tissue matrix underlying the membrane are applied in a coordinated fashion with pressure or suction from within the reservoir attached to the outer surface.

Various embodiments of the pressure modulation and flux enhancement device of this invention may be used to perform flux enhancement. Preferably, the devices would have at least one flux enhancement cell, and certain preferred embodiments would comprise multiple cells joined into a single array. In a multi-cell array, the flux cells may be arranged to work synchronously (e.g., by "parallel" cell function, delivering the permeant(s) from a plurality of cells at the same time), for example by synchronous control of individual actuators or by use of actuators which act on multiple cells. Such devices may be used to administer a single permeant, particularly when a large dose of the permeant is required, or to administer different permeants, where combination therapy is desired. Alternately, multi-cell devices may be arranged such that the various cells act asynchronously or even perform different functions. For example, a multi-cell device may comprise cells with different drugs which are administered on different schedules, or may comprise cells with different functions, such as a device comprising cells for delivery of a permeant as well as cells for sampling of fluid from the tissue matrix.

Figure 21:
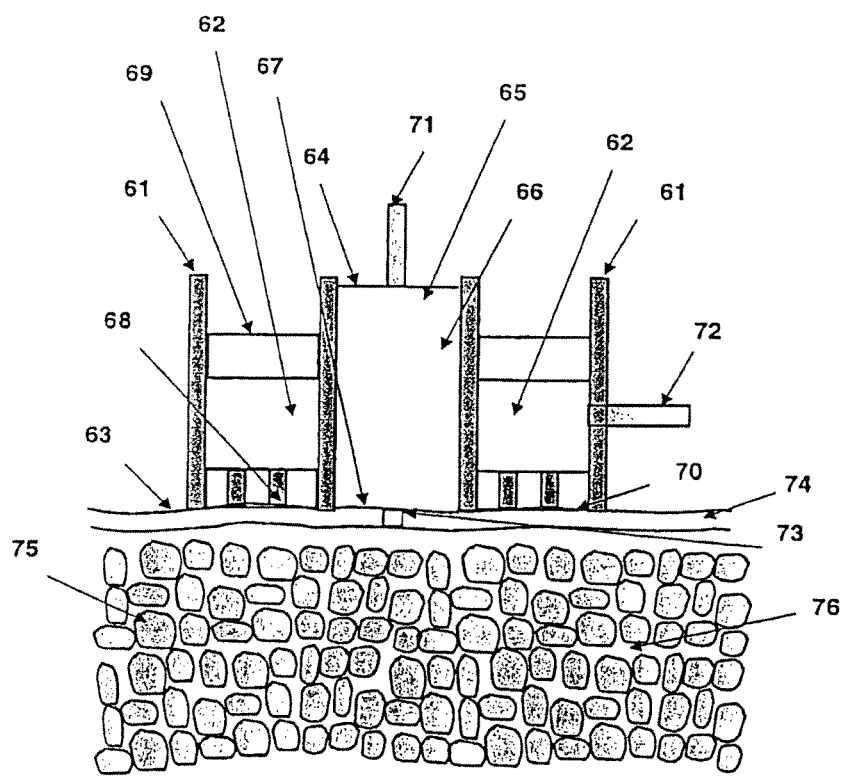
FIG. 21 shows one embodiment of a single cell flux enhancement device.

The structure of an embodiment of a single cell of a flux enhancement device of this invention is represented in FIG. 21. Generally, a single flux enhancement cell would have an outer wall or an outer annulus (61) defining a cell cavity (62), with the cavity open at least one end. This open end interfaces with the biological membrane (74) having a micropore (73) during use of the device. The outer wall is typically in the shape of a hollow cylinder having at least one open end, although polygonal cross-sections are also contemplated. The outer wall is substantially upstanding, and has an edge bounding the cavity (63, the "membrane interface 10 edge"). A reservoir (64) defining an inner cavity or a central portion (65) is movably contained in the cavity. In devices intended for administration of a permeant, the reservoir contains the permeant (66). The reservoir has an outlet (67), which is oriented towards the open (membrane interface) end of the cavity. In certain embodiments, a compliant membrane (68) spans the gap between the reservoir and the outer wall at the membrane interface end of the cavity. An additional compliant membrane (69) may also be included to form a pressure chamber defined by the reservoir wall, the outer wall, and the compliant membranes. The compliant membrane may additionally be coated with an adhesive (70), to promote a seal with the biological membrane. In other embodiments, the membrane interface edge of the outer wall, and the end of the reservoir with the outlet are coated with an adhesive. The reservoir and the outer wall may additionally comprise controllable pressure ports (71,72), through which the pressure in the cell cavity and inner cavity, respectively, maybe modulated. Underneath the biological membrane (74) is cell matrix (75) and biological fluid (76) in the space between the cell matrix (75).

The principle of the method of operating a flux enhancement device of this invention could be explained by an analogy wherein the skin tissue is replaced by a porous sponge upon which one side has had a non-porous, flexible membrane bonded to it. This membrane will represent the barrier layer of the skin tissue, which in the human subject is comprised of the stratum corneum. If a small hole is formed in the membrane, and then a liquid reservoir is placed over this, surely some of this liquid will infuse into the sponge beneath. However, once the sponge becomes fully saturated with fluid, a condition analogous to the ~90% water content dermis in human skin, this initial flux will stop and any further molecular flux from the outside into the sponge will be driven by diffusion alone due to concentration differences of selected compounds between the fluid in the reservoir and that in the sponge. As previously mentioned the case of animal (or human) skin, it is fully saturated with fluid to start with, so creating the micropore and placing the fluid reservoir over it limits the flux through the opening to that due to a concentration gradient driven passive diffusion process.

In one embodiment of this invention, the flux enhancement device is operated as shown sequentially in FIG. 22. FIG. 22a shows the initial 'neutral' stage of the systems pressure modulation cycle. FIG. 22a shows a single cell of a flux enhancement device, which could be a single-cell or a multiple-cell flux enhancement device. The single cell is adhered to the skin surface of the biological membrane by an adhesive.

FIG. 22b shows the blanching, or second, stage of the pressure modulation cycle. While gradually increasing the pressure in the reservoir, the entire area of the biological membrane surrounding the micropore(s) is depressed into the underlying skin tissue by pushing the central portion. As the force pushing the central portion increases, it forces the device to assume a conical shape, pressing into the targeted tissue, as shown in FIG. 22b. This produces two effects. First, by pushing the device on the biological membrane, the seal between the fluid reservoir and the skin surface becomes stronger, allowing a higher pressure to be maintained within this reservoir minimizing the possibility of a fluid leak. Second, the cell matrix under the skin tissue is compressed, forcing much of the fluid trapped within it between the cells out into the neighboring areas. In the case of human skin, this second effect is easily observed as the 'blanching' of the tissue when pressure is applied and then quickly removed. This could be easily demonstrated by pressing a fingertip firmly into the fleshy underside of ones forearm and then quickly removing it. The site most recently under compression is clearly whiter than the surrounding skin on a human subject.

FIG. 22c shows the tissue expansion, or third stage of the pressure modulation cycle. The central portion of the device is now pulled away from the skin tissue surface while the compliant annular portion is kept attached to the surface of the skin by a suitable adhesive, a mild pneumatic suction or vacuum, or some combination of these methods. Simultaneously, the pressure in the reservoir is dropped to ambient levels to ensure no leaks are formed from the central reservoir holding the drug payload. At this time the decompressed state of the recently blanched skin cell tissue matrix directly beneath the micropore would induce fluid from the drug reservoir to flow through the pore into these skin tissues beneath the porated surface.

FIG. 22d shows return to neutral, or fourth stage of the pressure modulation cycle. The central portion of the device surrounding the micropore(s) is now returned back to the neutral position, while simultaneously increasing the pressure in the reservoir slightly, as allowed while ensuring that no leaks occur. At this point, the permeant which had flowed into the cell matrix immediately beneath the micropore(s) in the previous steps, would now be induced to flow further away from the entry point into the larger volume of surrounding tissue and ultimately into contact with the capillaries whereupon it could then be absorbed into the blood stream if desired. Repeating this cycle would allow more and more fluid to be pumped into the tissue.

Suitable adhesives for attachment to the skin surface could include any one of the large number of existing, medical grade adhesives used in bandages, dressings, and transdermal patches current being produced. Many manufacturers, such as 3M, Avery, Specialty Adhesives, and the like, build adhesives specifically designed for this sort of application. Preferably, the adhesive chosen will have enough tackiness to attach the device to the tissue surface for the extent of its useful application, which could range from a few minutes to several days, and yet allow a painless removal when the system is spent. By combining a controlled application of suction to assist in this attachment process, a much less aggressive, and more people friendly adhesive can be used. When suction is used for assisting the attachment process, the adhesives stickiness properties become less important, however its ability to form a pneumatic seal, to contain the suction becomes more important. Clinical studies have demonstrated that when suction is used in conjunction with an adhesive, even very low performance adhesives, such as those used in the 3M product 'Post-Its', could be used effectively, supporting a completely painless, non-traumatic removal of the system whenever desired.

The compliant portions of the device, designed to interface and attach to the tissue surface maybe formed from compounds such as, but not limited to, silicone rubber, latex, vinyl, polyurethane, plastic, polyethylene or the like. The less flexible, or rigid portions of the device make be from any suitable, formable, material, such as metal, plastic, ceramic or the like. Preferably, materials that could be molded have some manufacturing advantages and, therefore, end product cost advantages as well. In some case, with a material such as silicone rubber, latex, vinyl, polyurethane, plastic, polyethylene or the like, both the flexible and more rigid portions of the system could be fabricated from the same material, simply by designing the dimensions of the various portions of the structure to allow the necessary flexing where needed and the required stiffness where needed as well. In this same general manner, a layered process could be utilized wherein similar, but slightly different compounds are introduced into the mold sequentially to give more flexibility in some areas and more stiffness in others, yet provide a good, seamless connection at the interface of the different 'mixes'. This type of selective variation in tensile properties could also be affected during the manufacturing process by selectively applying curing energy to different portions of the whole structure at different rates and amounts. For example, by irradiating with gamma rays, or ultraviolet light, one could form a greater number of cross-links in a polymer compound, dramatically changing its material properties across the same piece of material which was initial formed as a single piece. One commercially available example of a simple structure which exhibits both very compliant, and sticky qualities on one side, and much stiffer, non-sticky properties on the other side of a single piece of silicone are the 'Corn Pads' manufactured and sold by 'Dr. Scholls' as a foot care product.

To coordinate the actions of the systems, a pre-programmed controller would generate the proper sequence of control signals to cycle the system through these different steps as many times as desired. The controller may contain a microprocessor which would generate the appropriate sequence of control signals to enable the different functions of the system in the desired sequence. A small pump(s), such as a small diaphragm or peristaltic pump could be engaged when needed to develop a suction or pressure. Alternatively, a small pressure reservoir such as a metal or plastic cylinder or bladder of compressed gas, or a pressure produced via the electrolysis of a liquid in a closed chamber, producing gas, could be used to supply pressure. Optionally, control over all aspects of the movement of the system could easily be achieved with a simple valving mechanism(s) to provide the microprocessor coordinated control of reservoir pressure/suction and the action of a controllable actuator to provide the requisite movement of the central reservoir relative to the outer portions of the structure during the compression/decompression cycles. With suitable additional valves and seals, one could utilize the suction and pressure sources to provide the depression/withdrawal, action of the central portion from the skin surface. In this manner, a single peristaltic pump mechanism, with one or more circuits, could be engaged in either the forward or reverse direction, generating either pressure or suction as required, with the proper design of the swept area of the different pump circuits, and optionally, appropriately sized pressure bleed ports and one way valves, the required, coordinated, sequence of suction, pressure and mechanical translation could all be performed by a system with a single peristaltic pump based moving part. As peristaltic pumps are by nature, a positive displacement mechanism, they are very efficient. Alternatively, these motive forces could easily be provided by a small motor(s) or actuator(s) under microprocessor control with appropriate linkage to coordinate movements to the device cycle.

If a suitably strong adhesive is used to attach the system to the tissue surface, the entire sequence of tissue compression-expansion could be achieved using only the mechanical deformation of the device and the attached tissue, with atmospheric pressure providing the only pressure in the delivery-reservoir/extraction-chamber. In this case, the compression cycle would be used to generate a sufficiently high internal pressure in the tissue matrix to exceed the ambient atmospheric pressure and thereby induce the outflow of an analyte, such as interstitial fluid, through the pore(s) into the extraction chamber.

To utilize this idea to extract analytes from an organism, one only need to apply the same basic series of steps but while maintaining the reservoir at a reduced pressure level to induce the out flux of interstitial fluid through the pore(s) into a sample chamber. Therefore, when the skin is distended into the decompression state, the cell matrix will fill with interstitial fluid and then when the inward compression portion of the cycle occurs, this matrix trapped fluid will be forced out of the tissue at the paths of least resistance, one of which will be the micropore(s) leading into the sample chamber. An improvement on the extraction application could be made if the downward pressure could be applied by starting at the outer reaches of the zone involved and then bring the pressure inward towards the pores. This directed increase in pressure would tend to force more fluid towards the micropore(s), rather than letting it escape into the surrounding tissue matrix. Similarly, a reversal of this radially applied pressure pattern could be used to enhance the delivery mode described previously.

To optimize the process for harvesting or delivery, it is beneficial to change the relative timing and duration of the different phases of the process. For example, for a given subject, it will take a specific amount of time for a given peak distention of the skin tissue matrix in the decompression cycle to be fully filled up with interstitial fluid. This time is dependent upon the subject's level of hydration, their individual skin tissue make-up, the viscosity of their interstitial fluid and other less obvious factors such as the local hydraulic permeability of the tissue matrix, the subject's blood pressure and the like.

Similarly, optimizing for delivery will involve reversing the radially directed variation of pressure from the harvesting sequence described previously, such that after the delivery reservoir has been allowed to give up some portion of its fluid payload into the micropore(s) and the tissue beneath, if the downward pressure could be applied sequentially from the center of the device, it will tend to flush the fluid out into the surrounding tissue matrix and away from the micropore(s) in a peristaltic fashion. The device could also use a plunger mechanism designed to come down and cover and thereby seal off the micropore(s), making this directional forcing even more pronounced. All of these features could readily be included in a low cost disposable system.

The manufacture of the entire assembled system of the flux enhancement device of this invention is through a single molded component of plastic or silicone or the like. Similarly, the size of scale of the system could be varied widely, ranging from systems which may contain all of the active elements shown in FIG. 21 within a small assembly only a few hundred microns across, to scaled up versions wherein these same functional components may take up an area up to 10 cm across. For the smaller versions, it may well be useful to incorporate a plurality of flux enhancement cells within a single integrated system, with each micro-pressure modulation system being deployed over a selected number of pores through the skin. FIGS. 23a and 23b show a cross-sectional schematic of a multi-chamber, micro-cell array that also incorporates a thermal poration element(s) at the skin contact point for each micro-cell. The multi-chamber, micro-cell array could operate by the method and principle illustrated in FIGS. 22(a-d).

Figure 24:
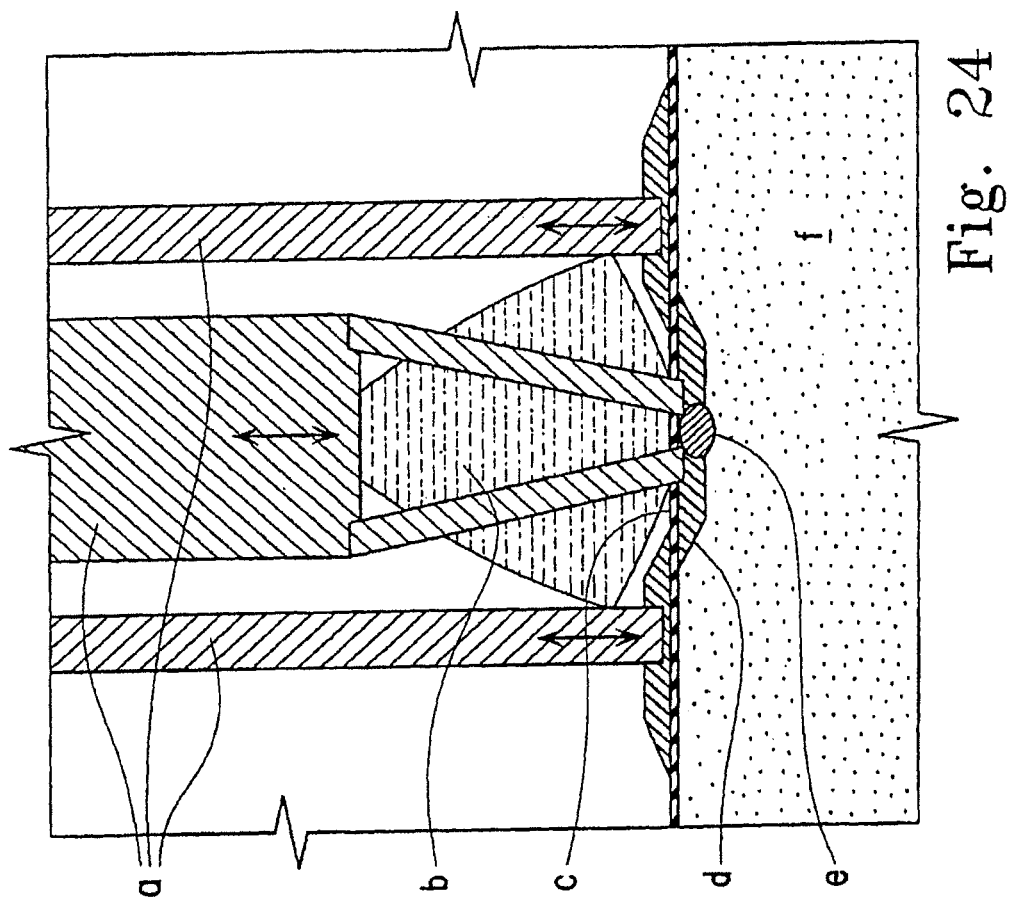
FIG. 24 shows a close-up view of a single pressure modulation micro-cell before activation.

FIG. 24 shows a close-up of a single micro-cell from that of the multi-chamber, micro-cell array of FIG. 23. The pressure modulation activation links (a) are shown connecting the central portion near the artificial opening and a separate pair of links connecting the outer annulus of the cell. By pressing the center links down in relation to the outer links, the blanching or compression phase of the cycle is achieved. Conversely, by pulling back on these central links while pressing the outer links down into the subject's skin, the decompression phase is formed. The permeant reservoir (b) is formed within the compliant, molded body of the patch and the pressure within this chamber is set by the relative deformation of the surrounding material as the skin deformation cycle is going through. Alternatively, a portal into each of these chambers could be molded into the patch body to facilitate and active and independent control of the pressure in the reservoir. This portal could also be used in the manufacturing process for filling the reservoir with the selected permeant(s). An adhesive disposed on the skin side of the thin film backing (c) and the conductive traces (d) could provide the necessary attachment to the skins surface. By using mold based manufacturing techniques, a patch-like system could be built which could be made to be only a few mm thick but covering an area of skin ranging from 1 to 20 square cm. This would allow the total system flux capacities to be scaled for each selected therapeutic compound. Also, a system which contains a plurality of micro reservoirs, each of which could be isolated from one another, is a needle-less delivery system able to delivery a plurality of different drugs, at different, yet controllable/programmable flux rates. The flux rates could be controlled or selected by several means including: setting the number of micro-pressure modulation cells for each drug, varying the both the rate and depth of actuation of various cells containing different drugs, varying the number of pores accessible by each cell, and so on.

An embodiment of the present inventive subject matter is a transdermal drug delivery device for forming a micropore in a tissue membrane of an animal, comprising a tissue interface layer, a plurality of reservoirs in communication with the tissue interface layer, and a controller for controlling the formation of the micropore by the at least one porator. The tissue interface layer includes a substrate and at least one porator, wherein said porator is located on or within said substrate. The plurality of reservoirs may include at least a first reservoir and a second reservoir. The first reservoir may contain a permeant composition to be introduced into the tissue membrane, while the second reservoir may contain an analyte extracted from the tissue membrane following poration of same. Further, the first reservoir may contain a first drug or therapeutically active agent and the second reservoir contains a second drug or therapeutically active agent, or the first reservoir may contain a drug or therapeutically active agent and the second reservoir may contain an excipient or other biologically safe diluent for reconstituting the drug or therapeutically active agent into a pharmaceutically acceptable delivery system. The porator in this embodiment may be of any type, material or form as has been discussed herein.

In a preferred embodiment, the porator comprises a plurality of porators, whereby a single porator is associated with a single reservoir, with the reservoirs containing a permeant composition or an analyte.

Another embodiment of the present inventive subject matter is drawn to a method of delivering two or more biologically active compounds to a patient in need thereof by way of a tissue membrane. The method comprises the steps of: a) forming at least one micropore in the tissue membrane by contacting a poration device with the tissue membrane and activating the poration device, thereby forming the at least one micropore; b) applying a first compound contained in a first reservoir of the poration device to the tissue membrane by way of the at least one micropore; and c) applying a second compound contained in a second reservoir of the poration device to the tissue membrane by way of the at least one micropore. The first and second compounds may be administered sequentially or simultaneously to the membrane. The first and second compounds may be first and second biologically active agents, or the first compound may be a first biologically active agent and the second compound may be a pharmaceutically acceptable excipient. Further, the first and second compounds may be mixed prior to being applied to the membrane.

A still further embodiment of the present inventive subject matter is drawn to a method of facilitating passage of biological compounds across a tissue membrane comprising the steps of: a) forming at least one micropore in the tissue membrane by contacting a poration device with the tissue membrane and activating the poration device, thereby forming the at least one micropore; b) applying a first compound contained in a first reservoir of the poration device to the tissue membrane by way of the at least one micropore; and c) extracting a second compound from the tissue membrane and storing the second compound in a second reservoir in the poration device. The steps of applying the first compound and extracting the second compound may be executed simultaneously, or the step of extracting the second compound from the tissue membrane may be carried out prior to the step of applying the first compound to the tissue membrane. Further, the method may comprise the step of analyzing the second compound and applying the first compound based on the analysis.

The design of the system, and the various structures and embodiments present as described also lend themselves to allow additional flux enhancement techniques to be utilized and combined with the basic pressure modulation/mechanical manipulation system such as electrotransport, electroporation, sonophoresis, chemical enhancers or the like. For example, if the body of the molded patch is formed with selected portions of it containing an electrically conductive polymer, this material, which will be in direct contact with the drug/permeant in the reservoir, could be used as the delivery electrode, while a separate, adjacent, conductive but electrically isolated portion of the patch could serve as the counter-electrode in an electro-transport enhanced delivery mode, By incorporating appropriate doping into this molded material to provide the functionality of an ion-exchange resin with biocompatible ions, it would also allow the electro-transport process to proceed without the concern of delivering unwanted molecules into the skin. These same conductive components could be used to electroporate the tissue accessible via the current conduit formed by the artificial opening in the skin's surface. The basic idea of combining electroporation with the thermal micropores is described in detail in U.S. Pat. No. 6,022,316, which is incorporated herein in its entirety. Similarly, with the conductive traces present on the skin-interface layer of the patch, they also could be used as electrodes for electro-transport, electro-poration, or impedance sensing between pores, a technique which has been shown to be useful to facilitate a closed loop, dynamic method for ascertaining whether each pore has been formed to the desired depth into the tissue matrix of the skin. Finally, by including an acoustic source, such as a sheet or layer of piezo-active or magneto-restrictive material, coupled to the top of the patch, the acoustic waves could be directed towards and through the reservoir, inducing higher drug/permeant flux rates through the pore into the skin. With acoustic energy, which could be used at all frequencies from sub-sonic to ultra-sonic, the patch material selection, and internal shape of the reservoir and other features of the patch could be used to very effectively focus and/or direct the acoustic energy as desired. For example, the curved conical shape of the reservoir (b) shown in FIG. 24, would have the effect of focusing a transverse acoustic wave propagating from the top of the figure towards the skins surface. With the correct curvature, the acoustic energy entering the reservoir could be focused into a small spot directly coincident with the pore formed at the bottom. Similarly, the mechanical linkage structures (a) shown in FIG. 24 could be used to form acoustic impedance mismatches and thereby direct by reflection at this boundary the acoustic waves towards the pores. This type of acoustic energy focusing could induce dramatic 'acoustic streaming' effects with local fluid velocities, as high as 50 cm/sec, and all directed through the pore and into the skin, with very low average sonic power levels.

The use of mode of sonic energy to induce acoustic streaming, as a method of transdermal flux enhancement is significantly different from the traditional mechanism attributed to sonic energy for this purpose. Whereas sonic and ultrasonic energy has been experimented with and used clinically for decades to increase the transdermal delivery of selected small to moderate molecular weight compounds, the general consensus amongst the scientific community regarding the actual mechanism of flux enhancement is that it is either inducing cavitation which causes microscopic vesicle openings in the various membrane and lipid bi-layers in the intact stratum corneum or that the sonic energy is inducing a local hypothermia condition, which is well known to increase the permeability of the stratum corneum and other skin tissues, particularly if the temperature exceeds the phase change point of the solid phase lipid layers in the stratum corneum of roughly 37° C. With the micropores present, an open channel with little or no hydraulic resistance is now presented to allow the influx of a drug formulation. The acoustic streaming effect allows high, local velocities and fluid pressures to be directed down these channels into the epidermis. It is noteworthy that this type of directed fluid velocity and. pressure into the micropores is much more advantageous than merely increasing the hydrostatic pressure within the delivery reservoir for the following reason. If one merely increases the pressure within the delivery reservoir, then, to hold this pressure and not induce a leak at the adhesive based junction between the patch and the skin surface, the adhesive used must be very aggressive. In clinical tests wherein patches have been attached to the subjects with cyanocrylic 'super-glue' adhesive, the continuous application of even a very low positive pressure of less than 1 psi, induces a leak to form within a few minutes. Anyone who has ever inadvertently glued their fingers together with this sort of 'super-glue' may find this surprising; as the inventors did when these experiments were done. However, upon examining closer where the leaks actually formed, the true situation is revealed. The following examples explain.

Example 7A

Constant Pressure Delivery

A moderately sized patch of 1 square inch total reservoir to skin area is applied, attached via adhesive to clean, dry, healthy human skin, on a non-calloused area such as the volar forearm or abdomen. The test patch has been formed from a clear plastic that allows continuous visual observation of the reservoir and the sealing surface occupying the ¼" wide outer perimeter of the patch. The reservoir is filled with an aqueous permeant, which for this experiment has been dyed a deep blue to assist in detection of any leaks from the chamber. The adhesive used is a cyanocrylic anaerobic 'super-glue' formulation, which has been applied and held under moderate but firm pressure for 5 minutes. The clear view afforded of the adhesive interface to the skin allows a good visual check for the quality and uniformity of the attachment. After ascertaining that the glue connection between the patch and the skin looks good, the dyed permeant solution is loaded into the delivery reservoir via an injection port, with a bleed port held open to allow the filling of the reservoir without generating any pressure. After ascertaining that there are no leaks present, with the bleed port closed, the injection port is now used to gradually apply a constant positive pressure to the delivery reservoir of 1 psi. This level of pressure is very low, less than what is typically present in a child's party balloon when inflated. Upon initial application of the pressure head, the skin beneath the reservoir stretches slightly and is bowed downward into the subject's body. One might expect an equilibrium condition to quickly establish itself whereon the distension of the skin reaches its maximum limit under this amount of force, and will stretch no further, but what was observed in multiple replications of this study is that the human skin is amazingly elastic under these conditions, and over the next few minutes, with pressure kept constant at 1 psi, the distension of the skin under the reservoir continues. The result of this is that the skin interface, at the inner surface of the glue attachment, is now being pulled almost perpendicularly away from the patch body. At this point, with the mild, but constant force pulling on the skin in this fashion, what begins to happen is that the stratum corneum itself begins to peel apart. The outermost layers of the stratum corneum are held together by a reinforcing network of the 'super-glue' which does penetrate slightly into this tissue, however, where this penetration stops, the binding forces holding the stratum corneum together are solely due to the natural, lipid based adhesion of the body acting as a 'mortar' between the 'bricks' of the keratinocytes, and it is this attachment which starts to breakdown and let go. By allowing the skin to stretch downward, away from the plane of the glue interface, the resistance to breaking the attachment is focused on a very few cells within the stratum corneum layer, rather than being spread out over a larger area. Once the stratum corneum begins to split in this fashion, as the pressure is being held constant, this split just continues until a leakage path is established to the outside of the patch. What this means is that regardless of how good an adhesive is used to attach this sort of patch to a human subject, if constant pressure is applied within the patch, it is almost impossible to stop the tissue splitting phenomena just described.

Example 7B

Constant Pressure Delivery

The same basic procedure of Example 7A is repeated, however, certain dimensions are now changed as follows. For the micropore to enable delivery, a practical density of micropores is to form a pore on 1-millimeter centers. For a 1-inch square total patch area, this would equate to 625 pores in a matrix of 25×25. Whereas, our experiments have indicated that essentially no medium to large molecular weight drug flux will occur through the unbroken skin between the pores, it seems wasteful to build a reservoir that covers the entire area. Instead, it makes better sense to construct the patch in a manner wherein each individual pore has a tiny micro-reservoir located directly over it. Preferably, if the bottom surface of the patch is formed such that the adhesive attachment to the skin runs right up to the edge of the pore which has been formed in through the stratum corneum layer, this provides the maximal total area of adhesive attachment to the skin and at the same time minimizes the total area of the skin which will be exposed to the constant pressure about to be applied. If each pore formed is 100 microns (0.0039 inch) in diameter, then the total skin area exposed to the pressure head is 625×3.142×(0.002)A2=0.0076 square inches. Comparing this number to the area presented by the previous example, of 1.0 square inches, the area is reduced by a factor, of 130:1. For each micropore/microreservoir, if the pressure head is brought back up to the same 1 psi, the peak force on the skin at each pore site would be only 0.000012 pounds, whereas in the first example the skin was being subjected to a total force of 1 pound, more than 80,000 time greater peak force. Under these conditions, it was found that it is possible to use a mild positive, steady pressure head to induce fluid flux through the micropores, for a limited amount of time up to about 20 minutes. However, even as in Example 7A, once any tearing away of the adhesive interface begins to occur, an avalanche effect comes into play wherein the peak pressure being presented to the skin starts to increase geometrically as the area exposed increases, and a leak failure is certain to occur. So, by merely redesigning the geometry of the patch interface to the skin, with specific attention to maximizing the attachment area and reducing the amount of un-porated skin exposed to the reservoir and the pressure head within the reservoir, a system could be constructed which does allow the use of a steady pressure gradient to induce a controlled delivery profile via the micro-pores for a period of time sufficient for many applications.

Example 7C

Modulated Pressure Delivery

Based on the results of the experiments described in Examples 7A and 7B above, a method for increasing the total duration possible of the pressure application was suggested. Basically, after examining the visco-elastic properties of the skin tissues, it was determined that if the patch design presented in Example 7B were used, but rather than holding a steady, constant pressure head overtime, that a cyclical pressure modulation should be applied. By allowing the pressure to drop to null periodically, two apparent advantages are realized. First, the continual stretching of the skin tissues is much more stressful on them than a pulsatile stretching process. By only giving relatively short pulses of pressure, the skin tissues themselves and more particularly the glue interface, are not stressed to the tearing point. Second, as the pressure induces a fluid flow via the micropore into the viable tissue matrix below, by dropping the pressure periodically, it allows the fluid perfused into these tissues to spread out into a larger area meaning that at the next pressure delivery cycle a more 'porous' tissue matrix will be presented. For the human skin, there are some natural resonant frequencies for which the time course of this sort of pressure modulation could be optimized. While there are clearly inter-subject variances in these resonance modes, our experimental work has indicated that varying the pressure cycle over a period of from 0.1 to 10 seconds works well on most subjects tested. It has also been noted that as the pressure cycle goes to shorter on periods, with an asymmetric duty cycle, that the peak pressures sustainable under these conditions start to rise dramatically, allowing peak pressures of more than 10 psi to be sustained, without tearing of the skin/adhesive interface if the on time is kept below 1 second and run at less than a 30% duty cycle.

Example 7D

Modulated Pressure Delivery

In addition to all of the embodiments described in Examples 7A, 7B and 7C, by incorporating an acoustic flux enhancement, and more particularly an acoustic streaming and focused sonic energy, an improved micropore based patch delivery system is realized. This improved delivery system uses a plurality of small, micro-reservoir chambers over each pore formed, wherein fluid flow and pressure is directed towards the pores, but no constant, steady pressure is created in the reservoirs themselves. By pulsing the acoustic energy focused on the pores with high peak power (0.1 to 100 watts/cm$^2$), short duration (0.0001 to 0.1 seconds) bursts at relatively low repetition rates (0; 1 to 50 Hz), short lived, transient pressure waves of several atmospheres, inducing both a radiation pressure fluid movement and acoustic streaming effect directing the permeant fluid through the pores and into the subjects body. Also, by applying the pressure to the fluid in this fashion, there is no net, constant pressure maintained in the reservoir, working to break down the adhesive attachment between the patch and the skin. In addition, whereas the peak power of the acoustic energy may be as high as 100 watts/cm$^2$ at the focal point, the low duty cycles used, typically 1% or less, reduce this level to an average power at this point of only 1 watt/cm$^2$, and keeping in mind that the actual area of the focal point is only around 100 microns across, or less than 0.0001 cm$^2$ for a total average sonic power level of only 100 microwatts actually being delivered, allowing for a very low cost, energy efficient system to be built.

All of these synergistic combinations of different active flux enhancement technologies have been described in detail in the cited granted and co-pending patents of these same inventors.

Example 8

Device which Combines Delivery and Monitoring

Figure 25:
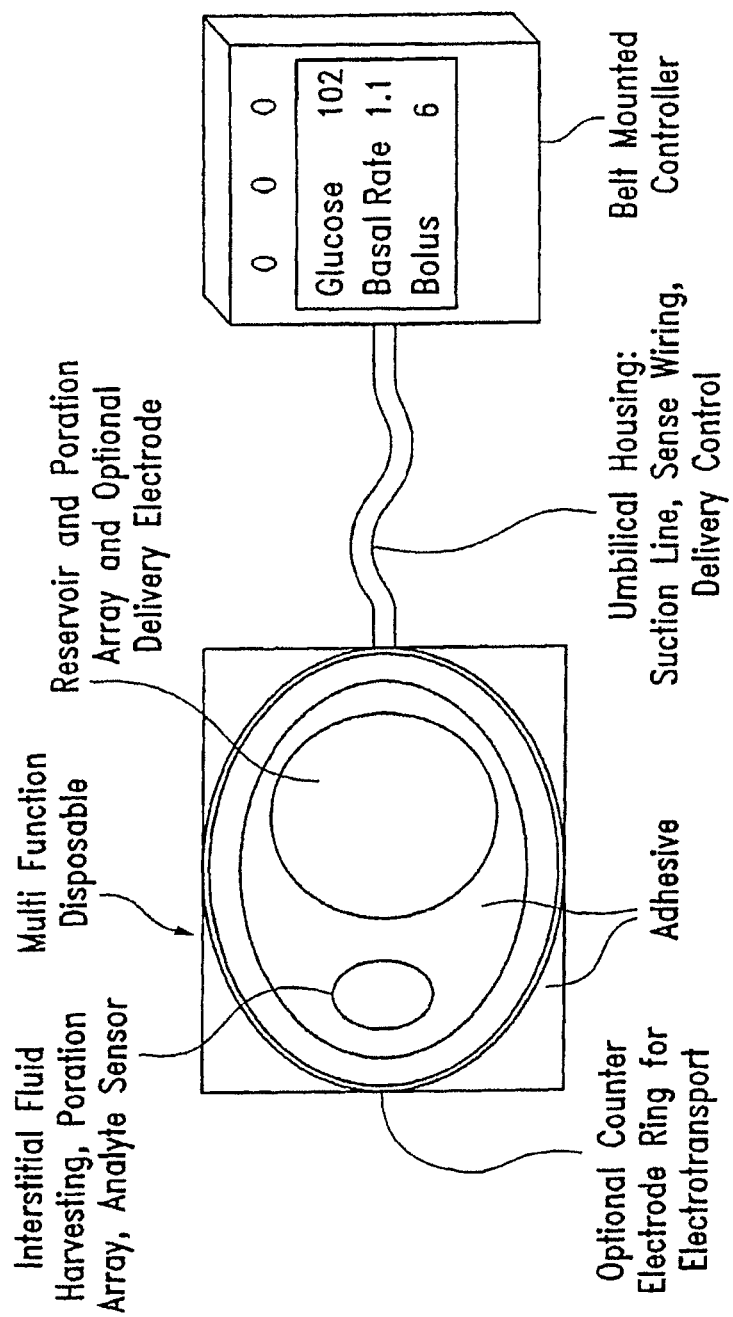
FIG. 25 shows an embodiment of an integrated device having a closed loop delivery and monitoring system with multi-function capabilities.

FIG. 25 shows a schematic illustration of a device for applying the micropore method simultaneously to both deliver a permeant into the subject and extract a biological fluid sample from the subject which is then analyzed for the lever of a selected permeant. The particular example shown in the figure is for a closed-loop insulin delivery/glucose monitoring application. The disposable patch contains two discrete sections, one devoted to the delivery of the insulin which contains all of the desired features of the various micropore based delivery methods and apparatus described herein, and the second section using the micropores to allow extraction of an interstitial fluid sample from which a glucose level could be measured. The controller module could be programmed with an algorithm designed to modulate the insulin delivery in a manner responsive to the measured glucose levels with the desired clinical goal of stabilizing the subject's glucose levels within the normal range of 80 to 100 mg/dl. The delivery algorithm could easily incorporate basal infusion rates and even pre-meal bolus delivery cycles just as today's latest insulin pump systems do in addition to relying solely on the measurement of the glucose levels. The disposable patch could be designed to last for several hours to several days, with the practical limit being driven by the useable life of the glucose sensor and the amount of insulin carried in the delivery reservoir. By allowing a direct measurement of the pharmacodynamic effect of the insulin delivery on the subject's glucose levels, a true, external, artificial pancreas has been realized. By using the micropores to establish both the delivery and extraction conduits, the system is also non-invasive as compared to the insulin pump which requires the installation of a physically invasive cannula into the subcutaneous layers of the skin and the lancet based blood draws to assess glucose levels. Whereas this example is focused on insulin infusion and glucose monitoring, the same basic concept can be applied to wide variety of therapeutic compounds that could benefit from a dynamically controlled delivery rate designed to achieve and maintain a specific pharmacokinetic/pharmacodynamic profile. Some good candidates for this sort of closed loop modulated-delivery system are; many of the chemotherapies being used which have a narrow window between when the optimal therapeutic effects are achieved and when the negative side effects become to oppressive to the subject; some of the psycho active drugs to control seizures; as a monitor on a on-demand patient controlled analgesia using opiate based compounds for treatment of chronic pain where a safety level threshold could be set which would not allow the subject to inadvertently over-medicate.

One embodiment of the present inventive subject matter is an integrated monitoring and delivery system comprising a delivery and extraction patch, a controller for actuating the porator array, thereby forming micropores in the tissue membrane, and an apparatus for analyzing the analyte. The apparatus contains an algorithm to determine a concentration of the analyte and control delivery of the permeant composition based on the analyte concentration. The delivery and extraction patch further comprises a first section comprising a first tissue interface layer and a first reservoir for storing a permeant composition to be applied to a tissue membrane. The first tissue interface membrane further comprising a substrate with a first porator array contained on or within the substrate. The delivery and extraction patch also includes a second section comprising a second tissue interface layer and a second reservoir for collecting an analyte from the tissue membrane for analysis. The second tissue interface membrane contains a substrate with a second porator array contained on or within the substrate. Optionally, the delivery and extraction patch includes an adhesive for adhering said patch to the tissue membrane.

A preferred embodiment of the present inventive subject matter is directed to a method of monitoring an analyte extracted from a patient and delivering a permeant composition to the patient. The method comprises the steps of: a) contacting a delivery and extraction patch to a tissue membrane of the patient; b) actuating poration of the tissue membrane using at least one poration array in the delivery and extraction patch; c) extracting an analyte from the microporated tissue membrane by way of at least one micropore array; d) analyzing the analyte to determine concentration of same within the tissue membrane; and e) delivering a permeant composition to the tissue membrane by way of at least one micropore array. In a preferred embodiment, the delivery and extraction patch comprises a first section comprising a first tissue interface layer and a first reservoir for storing a permeant composition to be applied to a tissue membrane, the first tissue interface membrane further comprising a substrate with a first porator array contained on or within the substrate, a second section comprising a second tissue interface layer and a second reservoir for collecting an analyte from the tissue membrane for analysis, the second tissue interface membrane further comprising a substrate with a second porator array contained on or within the substrate, and an adhesive for adhering the patch to the tissue membrane.

The inventive subject matter contemplates the first and second porator arrays of the above apparatus and method being the same porator array, or different porator arrays. Each of the porator arrays are each selected from the group consisting of a probe element, an electro-mechanical actuator, a microlancet, an array of micro-needles or lancets, a thermal energy ablator, a sonic energy ablator, a laser ablation system, and a high pressure fluid jet puncturer. Further, each of the reservoirs further comprise: a) a top layer; b) a middle layer that has at least one cavity for storing a drug or other permeant composition to be applied to the membrane in the first reservoir, and for accepting the analyte in the second reservoir; and c) a bottom layer, the bottom layer containing pores through which the drug is applied to the tissue membrane in the first reservoir, and through which the analyte is extracted in the second reservoir. In addition, the porator material may be constructed or produced as taught herein.

Example 9

Direct laser machining of planar arrays of poration elements

Figure 26:
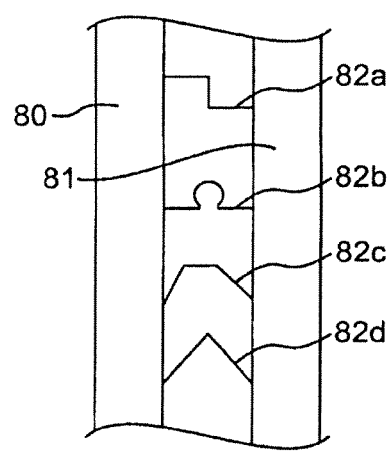
FIG. 26 shows a photomicrograph of an Actuated Planar array of microporation elements fabricated by direct laser machining of a tungsten film.
Figure 27:
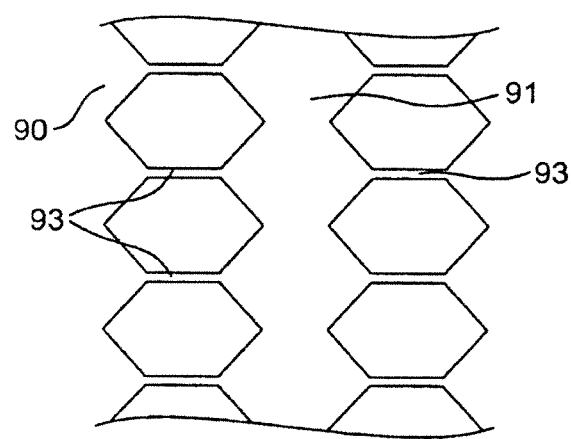
FIG. 27 shows a photomicrograph of a series/parallel interconnected planar array of microporation elements fabricated by direct laser machining of a tungsten film.

FIGS. 26 and 27 show two different design examples of how a functional planar array of poration elements could be fabricated using the direct laser machining methods described herein. In FIG. 26, the poration elements (82a-82d) could be fabricated with a kinked-loop shape. In general, the poration elements will be of the shape of any one of elements 82a to 82d; however, for ease of illustration, the different shapes are shown on the same planar array. In addition, other shapes not illustrated herein are also contemplated, as the shapes indicated are only for illustrative purposes and are not meant to be limiting. The shape will force the element, when heated by passing a current pulse through it, to bend upward, away from the supporting substrate, towards the biological membrane to be porated. The conducting traces (80 and 81) allow the current source to be delivered to the poration elements (82) in a parallel fashion, connecting simultaneously to the three elements shown in this figure.

FIG. 27 shows a similar array of planar poration elements (93) however not of the actuated design. The conductive traces (90, 91 and 92) connect the poration elements in this array in a series parallel circuit. In this fashion all eight poration elements (93) could be activated by passing the current pulse from conductive trace (90) to conductive trace (92), alternatively, either group of four elements connecting to the central conductive trace (91) could be activated as a group of four by selectively applying current between either traces (90) to (91) or between (91) and (92). Both examples shown in these photomicrographs of these device designs were fabricated by starting with a 50-micron thick tungsten alloy film, which was then cut to the final dimensions shown through a direct laser machining process. The individual poration elements each have a nominal width of 50 microns. For the tungsten alloy used in these devices, a poration element having the roughly square cross-section of 50 microns by 50 microns could be thermally cycled to greater than 1000° C. by passing a square wave current pulse through it having an amplitude of 1 amp, and a duration of 0.001 to 0.003 seconds. Other dimensions are contemplated with different materials, for example resistive elements made of copper may have different dimensions based on its conductive properties.

Example 10

Disposable Patch System

Figure 28:
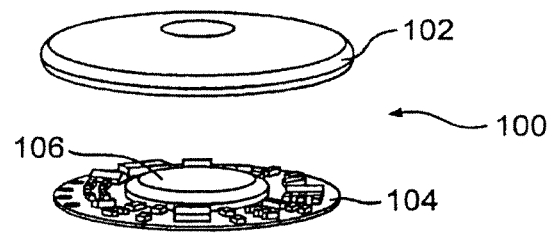
FIG. 28 shows an actuator section of a poration device.

FIG. 28 shows the actuator section of the device. The actuator section 100 consists a case 102 that houses a electrical circuit board 104, an actuator button 106, and a battery, not shown. The battery is a flat coin shaped cell. The electrical circuit provides a pulsed electrical current when the button is pressed. The bottom surface of actuator section has two exposed electrodes that are not shown.

Figure 29:
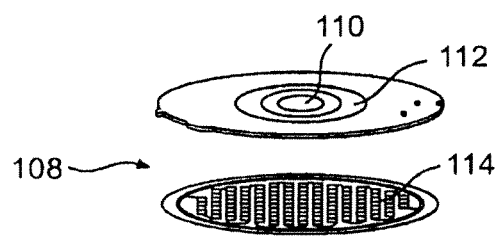
FIG. 29 shows a porator section of a poration device

FIG. 29 shows the microporator section of the device. The top surface of the microporator section 108 has two electrical contact areas 110 and 112. The contact areas are electrically insulated from each other. The top surface also has an adhesive area so as to permit attachment to the actuator section and contact between the actuator section electrodes and the contact areas 110 and 112.

On the bottom surface of the microporator section 108, there is exposed an array of 80 resistive elements, 114, spaced over an area of one square inch. The array of resistive elements is connected to the contact areas 110 and 112 so that electrical energy is passed from the actuator section to each of the resistive elements. The elements are expose such that they can be brought into intimate contact with body tissue without excessive pressure.

The elements are capable of conductively delivering thermal energy via direct contact to the tissue and act as heated probes to cause the ablation of a portion of the tissue membrane. The ablation of tissue forms micropores in the skin. The micropores formed have a diameter of about 50 microns and a depth of about 50 microns.

The resistive elements are straight bars with a cross-sectional area of about 625 square microns and have a length of 450 microns. When an electrical current pulse is applied to each element, the pulsed element is rapidly brought to a temperature of about 450° C. The array of resistive elements is connected in parallel to the current pulse source. The pulse duration is from 1 to 5 milliseconds; The bottom surface of the microporator section also has an adhesive area to facilitate maintaining the resistive elements in intimate contact with the body tissue. The microporator section has cover release liners on the adhesives areas on the top and bottom surfaces for protection. These covers are removed prior to use.

Figure 30:
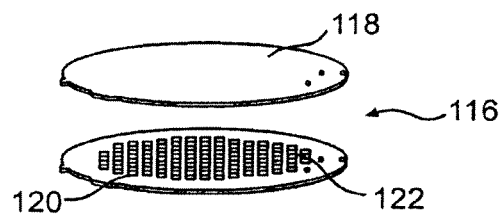
FIG. 30 shows a reservoir patch that is applied to the body tissue after the poration is accomplished.

FIG. 30 shows a reservoir patch 116 that is applied to the body tissue after the poration is accomplished. The patch consists of top layer 118, a middle layer 120 that has a cavity or cavities 122 for containing the drug and a bottom adhesive porous layer (not shown) for attachment to the body tissue over the porated area. The patch has additionally a cover layer attached to the bottom porous layer for protection and to retain the drug within the cavity behind the porous layer. This cover is removed prior to use.

After porating an area of the skin using this device, the microporator section 108 along with actuator section 100 are removed from over the porated area. The cover on the reservoir patch 116 is removed and patch 116 containing the drug is applied to the porated area of the skin tissue. The drug moves through porous layer of the patch and contacts the outer skin. The drug then diffuses through the micropores in the porated area of the tissue into the body over a period of time. This period of time may be minutes or days as appropriate for the specific drug and use indication for the drug.

A preferred embodiment is drawn to a poration system comprising a porator array having at least one porator and an actuator. The actuator comprises an outer body defining a top of the actuator and containing a cavity, a controller board comprising driving electronics and a battery, the controller board being positioned within the cavity, and an interface connection port for receiving the porator array.

A further embodiment of the present inventive subject matter is an integrated poration device as described above. The integrated poration device comprises an actuator, a porator array, and a reservoir patch. The reservoir patch is applied to the microporated area of the tissue membrane after poration. The actuator further comprises an outer body containing a cavity and defining a top of the actuator, a controller board comprising driving electronics and a battery, and being positioned within the cavity, and an interface connection port for receiving the porator array and containing an anode and a cathode. The porator array comprises a top surface, with a removable adhesive attached to the top surface. The top surface contains two concentric electrical contact rings for contacting the interface connection port at the anode and the cathode upon removal of the adhesive layer. The porator array also comprises a bottom surface comprising a tissue interface membrane and a release liner removably attached thereto.

A further embodiment is drawn to a poration system comprising a porator array comprising at least one porator and an actuator. The actuator comprises an outer body defining a top of the actuator and containing a cavity, a controller board comprising driving electronics and a battery, the controller board being positioned within the cavity, and an interface connection port for receiving the porator array.

The tissue interface layer further comprises a substrate with at least one porator contained on or within the substrate, and the bottom surface further comprises an adhesive layer for attaching the porator array to a tissue membrane.

Additionally, the reservoir patch further comprises a top layer, a middle layer that has at least one cavity for containing a drug or other permeant composition to be applied to the membrane, and a bottom layer, the bottom layer containing pores through which the drug is applied to the tissue membrane, and the bottom layer containing an adhesive for attachment of the reservoir patch to the microporated area of the tissue membrane. The reservoir patch may also include a cover layer attached to the bottom layer to retain the drug in the middle layer until the patch is applied to the tissue membrane. The device may include a control button for initiating poration of the tissue membrane.

The present inventive subject matter is also drawn to a method of using the above devices for monitoring of analytes and delivery of permeant compositions based on the analysis.

The method comprises the steps of: a) contacting the above device to a tissue membrane of the patient; b) actuating poration of the tissue membrane using at least one poration array in the delivery and extraction patch; c) extracting an analyte from the microporated tissue membrane by way of at least one micropore array; d) analyzing the analyte to determine concentration of same within the tissue membrane; and e) delivering a permeant composition to the tissue membrane by way of at least one micropore array. In an alternative embodiment, the device may be used to deliver two or more biological substances to a patient in need thereof.

In a still further embodiment, the present inventive subject matter is directed to a method of manufacturing the above poration device. The method comprises the steps of: a) forming an outer body defining a top of the integrated poration device, the outer body containing a cavity; b) assembling a controller board comprising driving electronics and a battery, and positioning the controller board within the cavity; c) assembling a reservoir comprising a top, side walls and a bottom, the top comprising a thin film top plate abutting a bottom of the controller board and positioning the reservoir within the cavity; and d) forming a tissue interface layer along the bottom of the reservoir, the tissue interface layer contacting a tissue membrane of an animal and containing at least one porator, and the tissue interface layer forming the bottom of the reservoir and of the integrated poration device.

Example 11

Two Step Locator Alignment System for Positioning a Drug Delivery Reservoir Over an Area of a Permeated Skin It advantageous to be able to form a planar array of micro-heaters using technologies which suitable for implementation in a high-volume production environment. A technique which yields a lower unit cost would be advantageous. Many currently used deposition techniques, lithographic techniques, and etching techniques are potential candidates for this application. It may be advantageous to form the micro-heaters in a manner which are supported on either end, but are not in contact the carrier substrate, which supports the planar array, elsewhere. This reduces conductive heat losses into the substrate and improves the geometry defining the interface between the heater elements and the outer skin tissues of an organism that the array is placed in contact with such that when the heaters are pulsed with energy, micropores are formed in these skin tissues, as described in U.S. Pat. No. 6,022,316.

Using a flexible substrate may also be advantageous both for the end user comfort and manufacturing efficiency. A flexible array of micro-heaters, elevated or otherwise, can be formed by starting with a thin flexible substrate such as polyethelene, polycarbonate, silicone, teflon, kapton, upsilon or other suitable material of this sort. Apply a layer of conductive material suitable for use as electric traces such as aluminum, copper, silver, gold, carbon, or the like. We have used layers of copper from less than 0.6 microns thick to more than 18 microns thick. These materials (ex: copper on kapton) are readily available from commercial sources such as Sheldahl, Dupont, Rogers, Gould as off-the-shelf items, typically used as a starting point for flexible circuit boards. On top of the conductive layer, apply a layer of resistive material such as titanium, titanium nitride, tantalum, tantalum nitride, chromium, a carbon compound, or the like. In the final array, the lower impedance conductive traces will be used to deliver a current pulse to the higher impedance micro-heaters will be formed primarily or the resistive material. 1) The use of selectively applied etch resist (photo resist, exposed through a mask could be used for this step) and an etchant, or an optical machining station, or other suitable micromachining techniques such as diamond milling, electron beam etching, or the like, to selectively remove portions of the conductive layers and resistive layer to create a pattern of feeder traces and resistors in the array. The use of a laser may be advantageous in some applications as it only requires one step and can be designed to form the programmed patterns rapidly in the resistive layer, as this layer is typically thinner than the conductive layer, and/or more photo-absorbant. The conductive traces will typically be several times larger in cross-section than the micro-heaters. 2) A final step which allows the formation of the elevated micro-heaters can be achieved by etching the entire array with a chemical to remove the conductive material but not the resistive material. This allows the resistive material to act as a protective layer (like a photo resist layer) over the traces. The etch time should be sufficient to remove all of the conductive material from between the traces, and produce some undercutting of the relatively wide conductive traces. This undercutting allows the etchant to completely remove the conductive material from beneath the relatively narrow micro-heaters. In this way, micro-heaters which are suspended from the substrate by the thickness of the conductive layer are formed.

Alternatively, or additionally, the substrate could be removed from beneath the micro-heater regions by applying a photo resist pattern and plasma, etching the back side of the array, or by laser ablation with a suitable laser source which is sufficiently absorbed by the targeted materials, i.e., remove the substrate but not the conductive layer, and then the conductive layer could be removed with an etchant which did not affect the resistive layer.

Alternative to traditional photo resist mask, an adhesive film can be applied to any layer, and a laser machining station used to remove material to form a mask for etching.

Alternative to the traditional, photo resist, shadow mask, an adhesive film can be applied to any layer, and a laser machining station used to remove material to form a mask for etching the desired pattern in the layers below the exposed portions of the mask.

Supported, elevated filaments could be formed by creating the conductive traces, applying an adhesive film such as kapton or a photo resist layer, then patterning the film with a laser machining station or patterning the photo resist with conventional photo exposure-developing methods and then etching so that small pads are formed bridging the gaps in the conductive traces. Filaments are then deposited through a mask so that they overlap these pads and touch the traces on either side. This technique would produce filaments that were the tallest items on the array, or rather filaments that protrude slightly from the surface of the array.

Unsupported, elevated filaments could be formed by creating the conductive traces, applying an adhesive film such as kapton or a photo resist layer, then patterning the film with a laser machining station or patterning the photo resist with conventional developing/etching methods so that small pads are formed bridging the gaps in the conductive traces. Filaments are then deposited through a mask so that they overlap these pads and touch the traces on either side. The photo resist pads or film pads could then be removed by chemical or plasma etching, or by $CO_2$ laser ablation from the reverse side of the array. This technique would produce filaments that were the tallest items on the array, or rather filaments that protrude slightly from the surface of the array.

Micro-heaters could be formed over the conductive layer or over preformed traces by sputtering or evaporating the desired thickness of resistive material through a shadow mask, for example of a copper or molybdenum foil, in a vacuum chamber.

Micro-heaters could be formed over the conductive layer or over preformed traces by depositing the desired thickness of resistive material through a shadow mask, for example of a copper or molybdenum foil, through the use of a combustion deposition technique such as, but not limited to, that described in U.S. Pat. No. 6,013,318.

Micro-heaters could be formed over the conductive layer or over preformed traces by conductive inks or powders and applied and formed using direct laser writing techniques, laser fusing of powders, electro-deposition, ink jet deposition or screen printing techniques which could be cured into a resistive layer to form the high impedance heater elements.

Micro-heaters could be formed over the conductive layer or over preformed traces by using a pick and place process which positioned individual preformed heater elements onto the array, and then mechanically and electrically bonded them as needed. This process would support the use of a variety of materials for the heater elements which may not be as easily adapted to the three previous process, and it would also allow the formation of heater elements which were mounted proud of the conductive traces.

The following ideas are related to the material composition and fabrication/production of the thermal component in the microporator device. These ideas are relevant to all microporation and poration devices discussed within this application. 1) The material composition of the device can be a bimetal foil such that the trace material is different from the microporation elements. 2) The materials can be a host of metals (and their alloys) including but not limited to: copper, aluminum, stainless steel, chromium, manganese, tantalum, nickel, platinum, evanohm, tungsten, titanium, gold, silver, titanium nitride. 3) The material can be thin films deposited by MEMs processes and their derivatives (sputter, electroplate, evaporation, CVD, CCVD, etc). 4) The component can be made from conductive inks or powders and manufactured using direct laser writing techniques, laser fusing of powders, electro-deposition, ink jet type deposition or screen printing techniques. 5) The substrate for the component can be thermo set (phenolics, polyesters, epoxies, urethanes, silicones, etc) or thermoplastic (polyethylene, polypropylene, polystyrene, PVC, Polytetrafluorethylene, ABS, Polyamides, polyamides, etc.), ceramic or stainless steel. 6) The material can also be in wire form. 7) The component can be manufactured using a variety of MEMs processes, including, but not limited to lasers, chemical vapor deposition, physical vapor deposition, combustion deposition, etc.

Example 12

Patch system of FIGS. 31-37

These shapes and figures are merely to be viewed as one representative version of these concepts for providing an alignment or registration mechanism which facilitates the application of an integrated poration device or a microporation system and then the subsequent step of applying a drug reservoir patch over the area in which the micropores are formed. The poration system could be thermal, mechanical, optical, chemical, electrical or acoustical.

Additionally, the two components comprising the porator array and the drug reservoir may be linked on the same substrate wherein a folding process can be utilized to bring the drug reservoir into contact with the porated skin area after removal of the activator, as is discussed below with respect to FIG. 38. After the reservoir is pressed into place, the locator components and the folding mechanism are removed, leaving only the drug reservoir behind for minimally affected area on the subject's skin.

Figure 31:
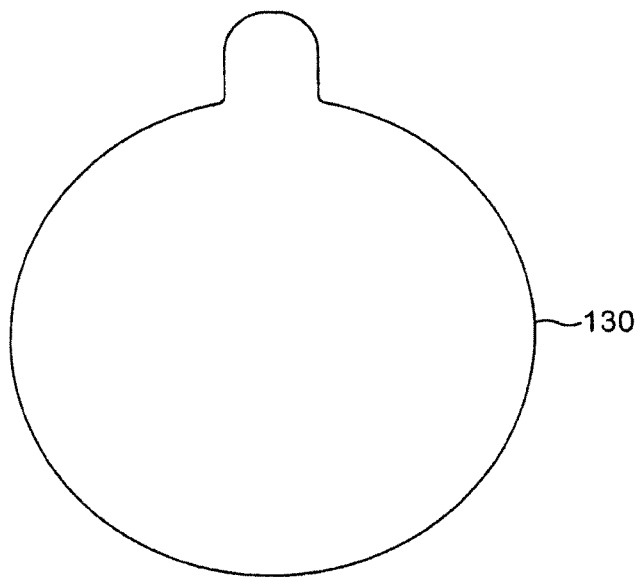
FIG. 31 shows a top view of a release liner for use in an embodiment of the present inventive subject matter.

FIG. 31 depicts a top view of a release liner 130 for protecting the top of a suitable porator array. Removal of release liner 130 exposes the top surface of the porator array which communicates with a reusable actuator/activator unit (not shown). Release liner 130 may be constructed of any suitable material which provides protection of the top of the porator array until it is time to connect the porator array to the actuator unit.

Figure 32:
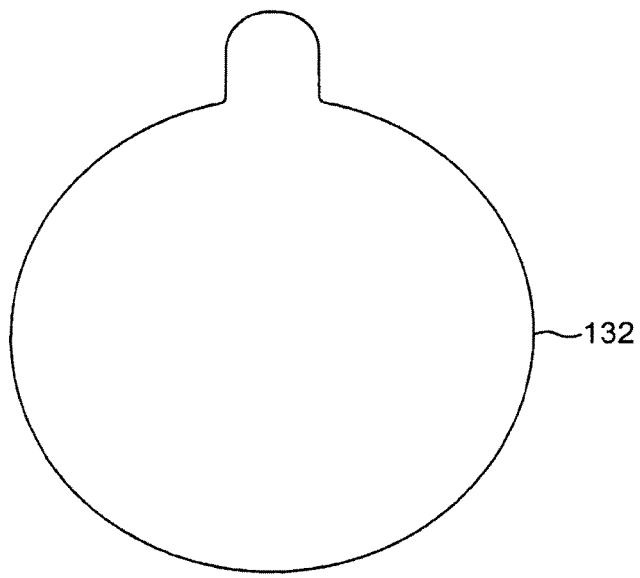
FIG. 32 depicts a top view of another release liner for protecting the bottom of a suitable porator array.

FIG. 32 depicts a top view of a release liner 132 for protecting the bottom of a suitable porator array. Removal of release liner 132 exposes the bottom surface of the porator array which is then attached to the tissue membrane to be porated. As with release liner 130, release liner 132 may be constructed of any suitable material which provides protection of the bottom of the porator array until it is time to attach the porator array to the tissue membrane.

Figure 33:
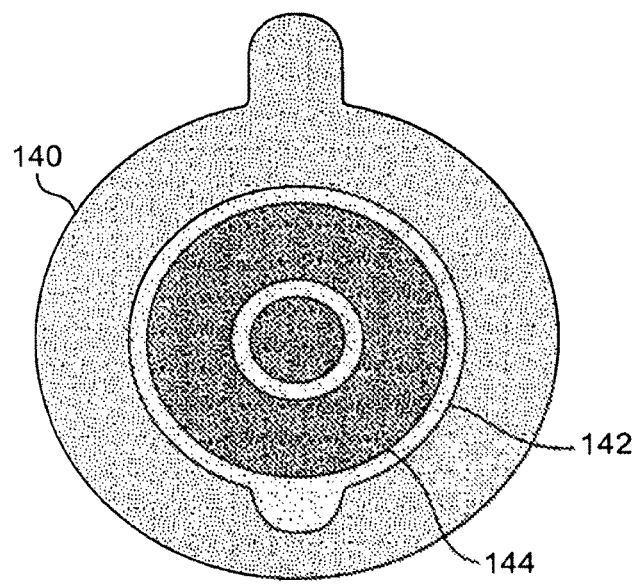
FIG. 33 depicts a top view of a porator array.

FIG. 33 depicts a top view of porator array 140 after the release liner as shown in FIG. 31 is removed. The top of porator array 140 physically and electrically connects with the actuator unit (not shown). As can be seen in the figure, the top of porator array 140 contains a pair of concentric electric contact rings 142 and 144. Electric contact rings 142 and 144 provide electrical communication between the actuator unit and porator array 140. The actuator unit contains anode and cathode contact pads on its bottom which align with electric contact rings 142 and 144. The electric current from the actuator unit is delivered to porator array 140 by way of electric contact rings 142 and 144. In addition, electric contact rings 142 and 144 aid in physically aligning porator array 140 with the actuator unit.

Figure 34:
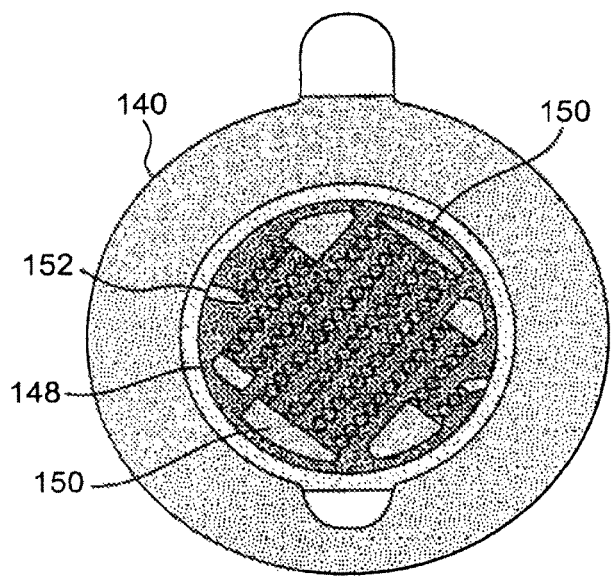
FIG. 34 shows a bottom view of one embodiment of a porator array.

FIG. 34 shows a bottom view of one embodiment of porator array 140, which is contacted with the tissue membrane to be porated. The bottom surface of porator array contains thermal poration elements 148 for effecting microporation of the tissue membrane. In this example, poration elements 148 are small filaments interconnecting wider current deliver traces 150. After application to the tissue membrane, an electric current pulse from the actuator unit (not shown) is delivered to porator array 140, actuating poration elements 148, and forming micropores in the tissue membrane. Porator array 140 also contains locator ring 152, which is a ring perforated in the material surrounding poration elements 148. The geometry for porator array 140 in this example is for illustrative purposes only and it is contemplated within the scope of the present inventive subject matter that other geometries and materials may be used.

Figure 35:
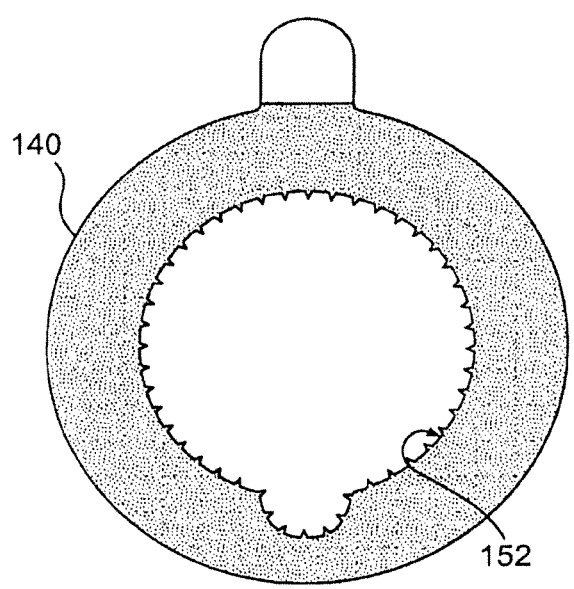
FIG. 35 shows a porator array after the poration elements have been removed from the locator ring.

Upon poration of the tissue membrane, poration elements 148 are removed from the tissue membrane by tearing along the locator ring 152. FIG. 35 shows porator array 140 after the poration elements have been removed from locator ring 152. Adhesive applied to this remaining portion of porator array 140 is of sufficient strength to cause the outer portion of porator array 140 to remain in place when the poration elements are pulled back from the tissue membrane. Similarly, the adhesive holding the poration elements to the tissue membrane is sufficient to pull away the poration elements away from the skin while breaking the perforations along locator ring 152.

Figure 36:
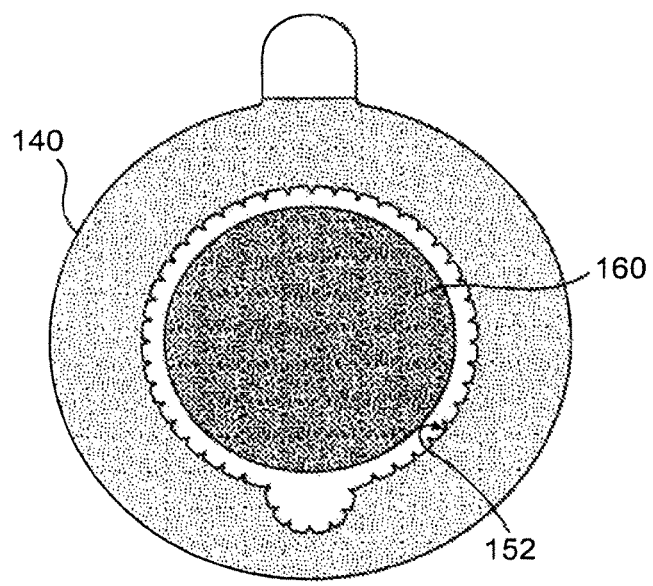
FIG. 36 depicts a drug reservoir patch applied to the porated area of the tissue membrane.
Figure 37:
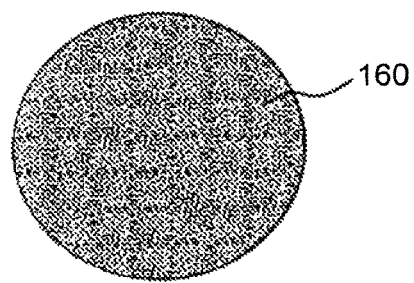
FIG. 37 shows reservoir patch following removal of the remaining portions of the porator array.

FIG. 36 depicts the application of a drug reservoir patch 160 to the porated area of the tissue membrane. As can be seen, drug reservoir patch, or reservoir patch, 160 is constructed of a size to fit within the area left behind in porator array 140 following removal of the poration elements. The reservoir patch is constructed of a top layer, a middle layer that has at least one cavity for containing a drug or other permeant composition to be applied to the membrane, and a bottom layer. The bottom layer contains small holes or pores through which the drug is applied to the tissue membrane and an adhesive for attachment of the reservoir patch to the porated area of the tissue membrane. FIG. 37 shows reservoir patch 160 following removal of the remaining portions of the porator array.

In a preferred embodiment, the actuator unit comprises an outer body containing a cavity and defining a top of the actuator, a controller board comprising driving electronics and a battery positioned within the cavity, and an interface connection port for receiving the porator array with the interface connection port containing an anode and a cathode.

Example 13

Figure 38:
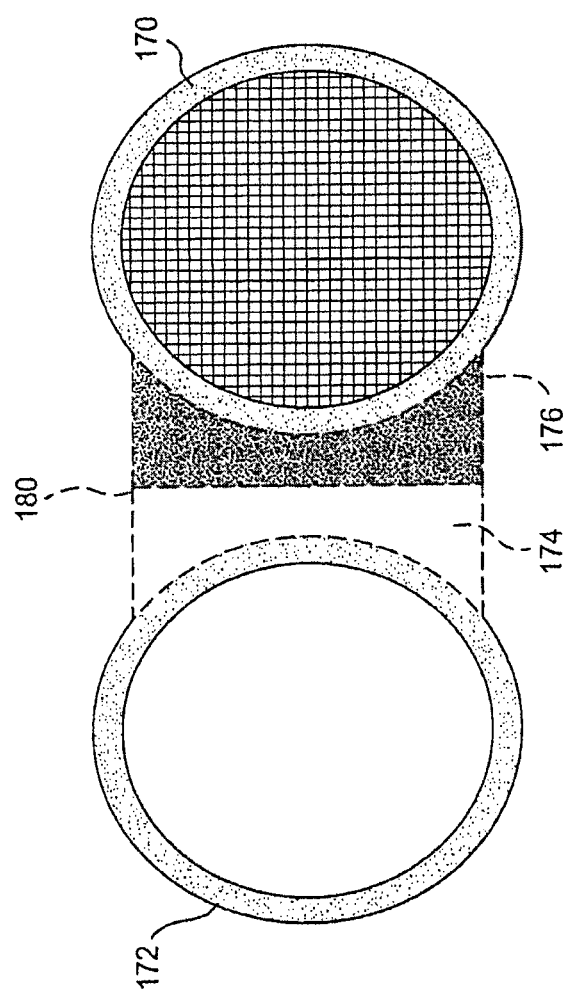
FIG. 38 shows a single piece disposable patch design.

Patch System of FIG. 38

FIG. 38 shows a single piece disposable patch design that incorporates in an integrated manner a poration array 170, which is held in registration to a drug reservoir patch or reservoir patch 172. The use of said system would be to first apply the porator array with an applicator device or actuation unit (not shown), upon removal of the applicator, the porator array 170 portion of the one-piece system would tear away from the rest of the system, leaving the reservoir patch and a folding extension tab 174 tab on the subject's skin. Reservoir patch 172 would then be applied over the site where the porator array had been applied by simply folding along a pre-formed crease line 180 in extension tab 170 and pressing reservoir patch 172 onto the porated site. The final step is the removal of the extension tab 174, which tears away from reservoir patch 172 along preformed perforated tear lines 176, leaving only reservoir patch 172 remaining on the subject's skin.

In a preferred embodiment, reservoir patch 172 is constructed of a top layer, a middle layer that has at least one cavity for containing a drug or other permeant composition to be applied to the membrane, and a bottom layer. The bottom layer contains small holes or pores through which the drug is applied to the tissue membrane and an adhesive for attachment of the reservoir patch to the porated area of the tissue membrane.

Further, the formation of the porations in the tissue membrane by the use of an actuation unit or other activation means may be accomplished by any device described herein and is not limited to any particular actuation unit.

A preferred embodiment is drawn to a drug delivery patch system comprising an actuator, a porator array, and a reservoir patch attached to an extension tab. The reservoir patch is applied to said microporated area of said tissue membrane after poration. The actuator comprises an outer body defining a top and containing a cavity, a controller board comprising driving electronics and a battery and being positioned within the cavity, and an interface connection port for receiving the porator array and containing an anode and a cathode.

The porator array further comprises a top surface, a bottom surface, an extension tab and a release liner removably attached to the bottom surface. The top surface includes a removable adhesive and containing two concentric electrical contact rings for contacting the interface connection port at the anode and the cathode upon removal of the adhesive layer. The bottom surface contains a tissue interface membrane comprising a substrate with at least one porator contained on or within the substrate. The bottom surface also has an adhesive layer for attaching the porator array to a tissue membrane. The porator array also includes an extension tab laterally and removably attached to the bottom surface. The extension tab further includes an adhesive applied on the bottom thereof, thereby allowing the extension tab to remain on the tissue membrane upon removal of the porator array.

The present inventive subject matter also includes a method for using such a device for administering a drug or other permeant to a patient in need thereof.

The advantages for using such a transdermal drug delivery patch system include:
1. The design eliminates any issues relating to having the porator array in any close contact with the reservoir patch.
2. It also ensures proper registration of the reservoir patch over the porated skin area after application of the porator array.
3. From the user perspective, what is actually two steps, (first porate, then apply the reservoir patch) becomes a single step of applying the porator array, then folding and tearing along the perforated lines to leave the reservoir patch in place, much like placing a letter in an envelope, then folding the flap to seal it, a pair of operations which are so intimately linked that they quickly become a single process in the minds eye.
4. From a marketing perspective, each application of the reservoir patch is inextricably linked to the use of one of the porator array disposables.
5. From a packaging consideration, a single foil pack can be used to contain the entire disposable porator array/reservoir patch assembly.
6. For manufacturing, the entire assembly can be formed and ETH/O sterilized if needed, then filled with the drug (aseptically if needed) prior to being sealed into the hermetic foil pack.

The inventive subject matter being thus described, it will be obvious that the same may be varied in many ways. Such variations are not to be regarded as a departure from the spirit and scope of the inventive subject matter, and all such modifications are intended to be included within the scope of the following claims.

The invention claimed is:

1. An integrated device for forming one or more micropores in a surface of a tissue of an animal comprising:
   a) a controller board connected to an energy source for actuating at least one probe element;
   b) a patch; and
   c) a tissue interface layer, said tissue interface layer containing at least one probe element, wherein each at least one probe element is a non-invasive heated resistive element that conductively delivers thermal energy to cause ablation of the tissue to a desired depth, thereby forming one or more micropores.

2. The integrated device according to claim 1, wherein said tissue interface layer comprises:
   a) a substrate, said at least one probe element being located on or within said substrate; and
   b) an adhesive layer for attaching said integrated poration device to said tissue.

3. The integrated device according to claim 2, wherein said substrate is selected from the group consisting of a woven material, a film, a supporting layer and a sheet.

4. The integrated device according to claim 1, wherein said at least one probe element comprises an array of probe elements.

5. The integrated device according to claim 1, further comprising a first control button for initiating poration of said membrane.

6. The integrated device according to claim 5, further comprising a second control button for initiating delivery of a permeant composition to said membrane or extraction of an analyte from said membrane.

7. A poration system comprising:
a) a porator comprising at least one probe element, wherein each at least one probe element is a non-invasive heated resistive element that is configured to conductively deliver thermal energy to cause ablation of a tissue membrane to a desired depth for the formation of a micropore;
b) a body defining a cavity;
c) a controller board comprising an energy source, said controller board being positioned within said cavity; and
d) an interface connection port for selectively receiving said porator.

8. The poration system according to claim 7, further comprising a patch, said patch being applied to said microporated area of said tissue membrane after poration.

9. The poration system according to claim 7, wherein said porator comprises:

a) a top surface, wherein a portion of the top surface contacts an anode and a cathode when the porator is in contact with the interface connection port; and
b) a bottom surface.

10. The poration system according to claim 8, wherein said patch is in proper registration over said microporated area of said tissue.

11. The poration system according to claim 7, a probe element of the at least one probe element is destroyed upon forming the micropore.

12. The poration system according to claim 7, wherein said porator is removably attached to said interface connection port.

13. The poration system according to claim 7, further comprising a control button for initiating poration of said tissue membrane.

14. The integrated device of claim 1, further comprising an outer body, wherein the outer body defines a top of the integrated poration device and wherein the outer body contains a cavity.

15. The integrated device of claim 14, wherein the controller board is positioned within the cavity.

16. The integrated device of claim 1, wherein said at least one probe element is in contact with said tissue for forming said one or more micropores.

* * * * *